United States Patent
Dimanche-Boitrel et al.

(10) Patent No.: US 10,426,758 B2
(45) Date of Patent: Oct. 1, 2019

(54) SIBIRILINE DERIVATIVES FOR USE FOR PREVENTING AND/OR TREATING DISORDERS ASSOCIATED WITH CELLULAR NECROPTOSIS

(71) Applicants: Institut National de la Sante et de la Recherche Medicale (INSERM), Paris (FR); Centre National de la Recherche Scientifique (CNRS), Paris (FR); Universite De Poitiers, Poitiers (FR); Sorbonne Universite, Paris (FR); Universite Claude Bernard Lyon 1, Villeurbanne (FR)

(72) Inventors: Marie-Thérèse Dimanche-Boitrel, Melesse (FR); Stéphane Bach, Sibiril (FR); Claire Delehouze, La Roche Maurice (FR); Yvette Mettey, Vincennes (FR); Peter Goekjian, Villeurbanne (FR); Arnaud Comte, Lyons (FR)

(73) Assignees: Institut National de la Sante et de la Recherche Medicale (INSERM) (FR); Centre National de la Recherche Scientifique (CNRS) (FR); Universite De Poitiers (FR); Sorbonne Universite (FR); Universite Claude Bernard Lyon 1 (FR)

( * ) Notice: Subject to any disclaimer, the term of this patent is extended or adjusted under 35 U.S.C. 154(b) by 0 days.

(21) Appl. No.: 15/768,388

(22) PCT Filed: Oct. 13, 2016

(86) PCT No.: PCT/EP2016/074638
§ 371 (c)(1),
(2) Date: Apr. 13, 2018

(87) PCT Pub. No.: WO2017/064217
PCT Pub. Date: Apr. 20, 2017

(65) Prior Publication Data
US 2018/0325876 A1 Nov. 15, 2018

(30) Foreign Application Priority Data
Oct. 13, 2015 (EP) ..................... 15306624

(51) Int. Cl.
*A61K 31/437* (2006.01)
*C07D 471/04* (2006.01)
*A01N 1/02* (2006.01)
*A61P 9/10* (2006.01)
*A61P 1/16* (2006.01)
*A61P 1/00* (2006.01)

(52) U.S. Cl.
CPC .......... *A61K 31/437* (2013.01); *A01N 1/0226* (2013.01); *A61P 1/00* (2018.01); *A61P 1/16* (2018.01); *A61P 9/10* (2018.01); *C07D 471/04* (2013.01)

(58) Field of Classification Search
CPC . A61K 31/437; A61P 9/10; A61P 1/16; A01N 1/0226
USPC .......................................... 514/300
See application file for complete search history.

(56) References Cited

U.S. PATENT DOCUMENTS

| | | | |
|---|---|---|---|
| 8,143,300 B2 | 3/2012 | Cuny et al. | |
| 2004/0053931 A1* | 3/2004 | Cox | C07D 471/04 514/249 |
| 2010/0041636 A1* | 2/2010 | Bhide | C07D 471/04 514/210.21 |
| 2013/0059850 A1* | 3/2013 | Walji | C07D 471/04 514/234.5 |
| 2014/0213554 A1* | 7/2014 | Wu | C07D 403/12 514/81 |
| 2015/0344473 A1* | 12/2015 | Du | C07D 471/04 514/210.18 |
| 2018/0312502 A1* | 11/2018 | Dimanche-Boitrel | C07D 471/04 |

FOREIGN PATENT DOCUMENTS

| | | |
|---|---|---|
| WO | 2008060907 A2 | 5/2008 |
| WO | 2011140164 A1 | 11/2011 |
| WO | 2014100620 A2 | 6/2014 |
| WO | WO-2017064216 A1 * | 4/2017 |

OTHER PUBLICATIONS

Conrad; Nat. Rev. Drug Discov. 2016,15, 348-366. (Year: 2016).*

(Continued)

*Primary Examiner* — Daniel R Carcanague
(74) *Attorney, Agent, or Firm* — Lerner, David, Littenberg, Krumholz & Mentlik, LLP

(57) ABSTRACT

The present invention relates to a compound of the following general formula (I) or a pharmaceutically acceptable salt and/or solvate thereof, for use as inhibitor of cellular necroptosis. The present invention also relates to a pharmaceutical composition comprising a compound of general formula (I), or a pharmaceutically acceptable salt and/or solvate thereof, for use for preventing and/or treating disorders associated with cellular necroptosis. The present invention also encompasses the use of a compound of the general formula (I) for organs preservation.

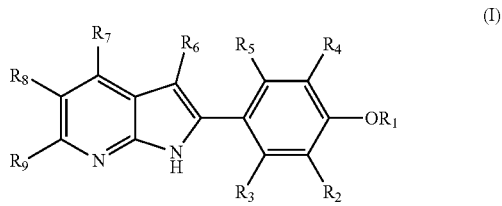

(I)

21 Claims, 10 Drawing Sheets

(56) References Cited

OTHER PUBLICATIONS

Harris; ACS Med. Chem. Lett., 2013, 4, 1238-1243. (Year: 2013).*
Leboho; Org. Biomol. Chem., 2014, 12, 307-315. (Year: 2014).*
Le Cann; The FEBS Journal 2017, 284, 3050-3068. (Year: 2017).*
Mettey; J. Med. Chem. 2003, 46, 222-236. (Year: 2003).*
Cho Y, McQuade T, Zhang H, Zhang J, Chan FK. RIP1-dependent and independent effects of necrostatin-1 in necrosis and T cell activation. PloS one. Aug. 10, 2011;6(8):e23209.
Degterev A, Hitomi J, Germscheid M, Ch'en IL, Korkina O, Teng X, Abbott D, Cuny GD, Yuan C, Wagner G, Hedrick SM. Identification of RIP1 kinase as a specific cellular target of necrostatins. Nature chemical biology. May 2008;4(5):313.
Degterev A, Huang Z, Boyce M, Li Y, Jagtap P, Mizushima N, Cuny GD, Mitchison TJ, Moskowitz MA, Yuan J. Chemical inhibitor of nonapoptotic cell death with therapeutic potential for ischemic brain injury. Nature chemical biology. Jul. 2005;1(2):112.
International Search Report for PCT/EP2016/074638 date Jan. 17, 2017, 3 pages.
Jagtap PG, Degterev A, Choi S, Keys H, Yuan J, Cuny GD. Structure-activity relationship study of tricyclic necroptosis inhibitors. Journal of medicinal chemistry. Apr. 19, 2007;50(8):1886-95.
Jouan-Lanhouet S, Riquet F, Duprez L, Berghe TV, Takahashi N, Vandenabeele P. Necroptosis, in vivo detection in experimental disease models. Seminars in cell & developmental biology Nov. 1, 2014 (vol. 35, pp. 2-13). Academic Press http://dx.doi.org/10.1016/j.semcdb.2014.08.010.
Linkermann A, Green DR. Necroptosis. New England Journal of Medicine. Jan. 30, 2014;370(5):455-65.
Miao, Benchun, and Alexei Degterev. "Methods to analyze cellular necroptosis." Apoptosis. Humana Press, Totowa, NJ Cahpter 6, pp. 2009. 79-93.
Strilic B, Yang L, Albarrán-Juárez J, Wachsmuth L, Han K, Müller UC, Pasparakis M, Offermanns S. Tumour-cell-induced endothelial cell necroptosis via death receptor 6 promotes metastasis. Nature. Aug. 2016;536(7615):215.
Takahashi N, Duprez L, Grootjans S, Cauwels A, Nerinckx W, DuHadaway JB, Goossens V, Roelandt R, Van Hauwermeiren F, Libert C, Declercq W. Necrostatin-1 analogues: critical issues on the specificity, activity and in vivo use in experimental disease models. Cell death & disease. Nov. 2012;3(11):e437.
Teng X, Keys H, Jeevanandam A, Porco Jr JA, Degterev A, Yuan J, Cuny GD. Structure-activity relationship study of [1, 2, 3] thiadiazole necroptosis inhibitors. Bioorganic & medicinal chemistry letters. Dec. 15, 2007;17(24):6836-40.
Wang K, Li J, Degterev A, Hsu E, Yuan J, Yuan C. Structure-activity relationship analysis of a novel necroptosis inhibitor, Necrostatin-5. Bioorganic & medicinal chemistry letters. Mar. 1, 2007;17(5):1455-65.
Wu Z, Li Y, Cai Y, Yuan J, Yuan C. A novel necroptosis inhibitor—necrostatin-21 and its SAR study. Bioorganic & medicinal chemistry letters. Sep. 1, 2013;23(17):4903-6.
Xie T, Peng W, Liu Y, Yan C, Maki J, Degterev A, Yuan J, Shi Y. Structural basis of RIP1 inhibition by necrostatins. Structure. Mar. 5, 2013;21(3):493-9.
Zheng W, Degterev A, Hsu E, Yuan J, Yuan C. Structure-activity relationship study of a novel necroptosis inhibitor, necrostatin-7. Bioorganic & medicinal chemistry letters. Sep. 15, 2008;18(18):4932-5.

\* cited by examiner

SIBIRILINE DERIVATIVES FOR USE FOR PREVENTING AND/OR TREATING DISORDERS ASSOCIATED WITH CELLULAR NECROPTOSIS

CROSS REFERENCE TO RELATED APPLICATIONS

The present application is a national phase entry under 35 U.S.C. § 371 of International Application No. PCT/EP2016/074638, filed Oct. 13, 2016, which claims priority from European Patent Application No. 15306624.6 filed Oct. 13, 2015, all of which are hereby incorporated herein by reference.

The present invention relates to sibiriline derivatives for use as inhibitor of cellular necroptosis. In particular, the present invention relates to sibiriline derivatives for use for preventing and/or treating disorders associated with cellular necroptosis.

Programmed cell death is a natural process for removing unwanted cells, such as cancer cells. Necroptosis is clearly distinct from apoptosis as it does not involve key apoptosis regulators, such as caspases, Bcl-2 family members or cytochrome c release from mitochondria. "Necroptosis" is a specialized biochemical pathway of programmed necrosis that depends notably on the serine/threonine kinase activity of RIPK1 (Receptor-Interacting Protein Kinase 1). It can be inhibited by necrostatin-1, an inhibitor of RIPK1 (U.S. Pat. No. 8,143,300).

Necroptosis may be activated upon stimulation by TNF-α (Tumor Necrosis Factor α), FasL (Fas ligand) and TRAIL (Tumor-necrosis-factor Related Apoptosis Inducing Ligand), and relies on the activity of two serine-threonine kinases, RIPK1 and RIPK3. TNF via TNFR1 (Tumor Necrosis Factor Receptor 1) leads to the formation of two sequential signaling complexes. The receptor-proximal complex I induces pro-survival signals through activation of NF-κB (Nuclear Factor—kappa B) and MAPKs (Mitogen Activated Protein Kinases), while the second cytosolic complex II signals two cell death pathways: (a) apoptosis, via formation of complex IIa including FADD (Fas-Associated Death Domain) that recruits caspase-8 and/or caspase-10 to activate a caspase cascade; (b) necroptosis, via activation of RIPK1 and RIPK3 kinases in a complex called the necrosome. TNF-α can induce necroptosis in Jurkat cells when FADD is deleted (Miao and Degterev, *Methods Mol. Biol.* 2009, 559, 79-93).

The ground-breaking finding that necroptosis is a genetically controlled process led to the hypothesis that this programmed cell-death is 'druggable', an emerging breakthrough that carries the potential to revolutionize every day clinical medicine (Linkermann and Green, *N. Eng. J. Med.* 2014, 370(5), 455-465). Indeed molecular targets, including RIPK1 (Receptor Interacting Protein 1), RIPK3 and MLKL (Mixed Lineage Kinase domain-Like), have convincingly been shown to contribute to multiple disorders where necroptosis is of central pathophysiological relevance, such as: ischemia-reperfusion injury in brain, heart and kidney, inflammatory diseases, sepsis, retinal disorders, neurodegenerative diseases and infectious disorders (Jouan-Lanhouet et al. *Semin. Cell. Dev. Biol.* 2014, 35, 2-13). More recently, it has been shown that human and murine tumour cells induce necroptosis of endothelial cells, which promotes tumour cell extravasation and metastasis (Strilic et al. *Nature* 2016, 536(7615), 215-218). Necroptosis can thus also be targeted in the treatment of human metastasis, the leading cause of cancer-related death in humans.

Only few RIPK1 inhibitors have been developed (Degterev et al. *Nat. Chem. Biol.* 2005, 1(2), 112-119, and *Nat Chem Biol.* 2008, 4(5), 313-321). Among them, necrostatin-1 (Nec-1) has been used to specifically inhibit several necrotic processes. However, RIPK1-independent effect of Nec-1 has been pointed out (Cho et al. *PLoS One.* 2011, 6(8):e23209), and Nec-1 is also an inhibitor of indoleamine 2, 3-dioxygenase (Takahashi et al. *Cell Death Dis.* 2012, 3:e437). Moreover, the stability of Nec-1 in vivo is very limited. Several structurally distinct necrostatins (Nec-3 (Jagtap et al. *J. Med. Chem.* 2007, 50(8), 1886-1895), Nec-4 (Teng et al. *Bioorg. Med. Chem. Lett.* 2007, 17(24), 6836-6840), Nec-5 (Wang et al. *Bioorg. Med. Chem. Lett.* 2007, 17(5), 1455-1465), Nec-7 (Zheng et al. *Bioorg. Med. Chem. Lett.* 2008, 18(18), 4932-4935)) and corresponding modifications have been reported. Recently, Nec-21, another potent Nec-1 analogue was reported to show an improved off-target profile (Wu et al. *Bioorg. Med. Chem. Lett.* 2013, 23(17), 4903-4906). One of the best stable RIPK1 inhibitor is Nec-1s (Nec-1 stable), which was shown to interact with a hydrophobic pocket of the kinase domain, hence stabilizing RIPK1 in an inactive conformation (Xie et al. *Structure* 2013, 21(3), 493-9).

There is therefore a need for new RIPK1 inhibitors with high potential, good stability and low toxicity.

The inventors of the present invention have thus discovered new sibiriline derivatives that inhibit the necroptotic cell-death. These compounds thus appear to be very attractive in therapy for preventing and/or treating disorders associated with cellular necroptosis. Besides, such compounds are also for use for the preservation and/or protection of biological materials such as cells, tissues, body fluids and organs, and of microorganisms, advantageously as a medical device.

Thus, the present invention relates to a compound of the following general formula (I):

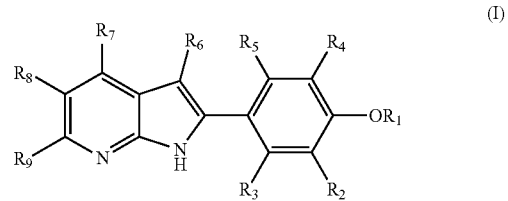

or a pharmaceutically acceptable salt and/or solvate thereof, wherein:
  $R_1$ is H, a $(C_1-C_6)$alkyl or a $(C_3-C_6)$cycloalkyl; or $R_1$ forms together with $R_2$ or $R_4$ a a heterocycloalkyl;
  $R_2$ to $R_6$ are, independently of one another, H or $OR_{10}$;
  $R_{10}$ is H or $(C_1-C_6)$alkyl;
  $R_7$ to $R_9$ are, independently of one another, H; halo; —$OR_{11}$, —$NR_{12}R_{13}$; —$C(O)NR_{14}R_{15}$; —$C(O)R_{16}$; —$R_{17}C(O)OR_{18}$; —$R_{19}C(O)R_{20}$; —$R_{21}NR_{22}R_{23}$; —$R_{24}OR_{25}$; —$R_{26}OR_{27}Si(R_{28})_3$; —$S(O)_2R_{29}$; —$OR_{30}C(O)OR_{31}$; —$OC(O)R_{32}$; —$C(O)OR_{33}$; —O—$SO_2$—$NR_{34}R_{35}$ or a group selected from $(C_1-C_6)$alkyl, $(C_2-C_6)$alkynyl, heterocycle, aryl, heteroaryl, —$(C_1-C_6)$alkyl-aryl, and —$(C_1-C_6)$alkyl-heterocycle, said group being optionally substituted with one or several groups selected from halo, —$OR_{36}$, —$NR_{37}R_{38}$, —$SR_{39}$, —$S(O)R_{40}$, —$SO_2R_{41}$, —$SO_2NR_{42}R_{43}$, —$OCOR_{44}$, —$NR_{45}COR_{46}$, —$NR_{47}C(O)OR_{48}$, —$CO_2R_{49}$, —$CONR_{50}R_{51}$, —OCONR$_{53}$R$_{54}$, —COR$_{55}$, nitro (—NO$_2$), cyano (—CN), oxo (=O), and a group selected from aryl, heterocycle and —(C$_1$-C$_6$)alkyl-heterocycle, said group being optionally substituted with one or several (C$_1$-C$_6$)-alkyl; and R$_{11}$ to R$_{55}$ are, independently of one another, H, halo, benzoylbenzyl, or a group selected from (C$_1$-C$_6$)alkyl, aryl, heteroaryl, heterocycle, —(C$_1$-C$_6$)alkyl-heterocycle, and —(C$_1$-C$_6$)alkyl-aryl, said group being optionally substituted with one or several groups selected from halo, CF$_3$ or (C$_1$-C$_6$)alkyl; or R$_{12}$-R$_{13}$, R$_{14}$-R$_{15}$, R$_{22}$-R$_{23}$, R$_{34}$-R$_{35}$, R$_{37}$-R$_{38}$, R$_{42}$-R$_{43}$, R$_{50}$-R$_{51}$, and/or R$_{53}$-R$_{54}$ may together respectively form a heterocycloalkyl, for use for preventing and/or treating disorders associated with cellular necroptosis.

For the purpose of the invention, the term "pharmaceutically acceptable" is intended to mean what is useful to the preparation of a pharmaceutical composition, and what is generally safe and non-toxic, for a pharmaceutical use.

The term "pharmaceutically acceptable salt or solvate" is intended to mean, in the framework of the present invention, a salt or solvate of a compound which is pharmaceutically acceptable, as defined above, and which possesses the pharmacological activity of the corresponding compound.

The pharmaceutically acceptable salts comprise:

(1) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and (2) base addition salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

Acceptable solvates for the therapeutic use of the compounds of the present invention include conventional solvates such as those formed during the last step of the preparation of the compounds of the invention due to the presence of solvents. As an example, mention may be made of solvates due to the presence of water (these solvates are also called hydrates) or ethanol.

The terms "(C$_1$-C$_6$)alkyl", as used in the present invention, refers to a straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "(C$_3$-C$_6$)-cycloalkyl", as used in the present invention, refers to a saturated hydrocarbon ring comprising from 3 to 6, advantageously from 5 or 6, carbon atoms, in particular the cyclohexyl, cyclopentyl, cyclobutyl or cyclopropyl group.

The term "(C$_2$-C$_6$)-alkynyl" as used in the present invention refers to a linear or branched hydrocarbon chain comprising at least one triple bond and comprising from 2 to 6 carbon atoms, e.g., such as an ethynyl or propynyl group.

The term "aryl", as used in the present invention, refers to an aromatic hydrocarbon group comprising preferably 6 to 10 carbon atoms and comprising one or more, notably 1 or 2, fused rings, such as, for example, a phenyl or naphtyl group, advantageously a phenyl group.

The term "—(C$_1$-C$_6$)alkyl-aryl", as used in the present invention, refers to an aryl group as defined above bound to the molecule via a (C$_1$-C$_6$)alkyl group as defined above. In particular, the —(C$_1$-C$_6$)alkyl-aryl group is a benzyl group.

The term "heterocycle" as used in the present invention refers to a saturated, unsaturated or aromatic hydrocarbon monocycle or polycycle (comprising fused, bridged or spiro rings), such as a bicycle, in which one or more, advantageously 1 to 4, and more advantageously 1 or 2, carbon atoms have each been replaced with a heteroatom selected from nitrogen, oxygen and sulphur atoms, and notably being a nitrogen atom. Advantageously, the heterocycle comprises 5 to 15, notably 5 to 10 atoms in the ring(s). Each ring of the heterocycle has advantageously 5 or 6 members.

According to a particular embodiment, the heterocycle is a saturated, unsaturated or aromatic hydrocarbon monocycle or bicycle (comprising fused, bridged or spiro rings, notably fused rings), each cycle having 5 or 6 members and 1 to 4, notably 1 or 2, carbon atoms having each been replaced with a nitrogen or oxygen atom, notably a nitrogen atom.

A heterocycle can be notably thiophene, furan, dioxane, dioxalane, pyrrole, imidazole, pyrazole, oxazole, isoxazole, thiazole, isothiazole, triazoles (1,2,3-triazole and 1,2,4-triazole), benzofuran, tetrahydrofuran, indole, benzothiophene, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, piperidine, piperazine, triazinane, morpholine, pyrrolidine, dihydropyridines, dihydropyrimidines (notably 1,2-dihydropyrimidine), dihydropyridazines, dihydropyrazines, dihydrotriazines, tetrahydropyridines, tetrahydropyrimidines, tetrahydropyridazines, tetrahydropyrazines, tetrahydrotriazines, etc.

The term "—(C$_1$-C$_6$)alkyl-heterocycle" as used in the present invention refers to a heterocycle group as defined above bound to the molecule via a (C$_1$-C$_6$)alkyl group as defined above. In particular, the —(C$_1$-C$_6$)alkyl-heterocycle group is a methylmorpholinyl or methylpiperazinyl group.

The term "heterocycloalkyl" as used in the present invention refers to a saturated heterocycle as defined above.

According to a particular embodiment of the present invention, the term "heterocycloalkyl" refers to a saturated hydrocarbon ring having 5 to 7 members, in which one or more, advantageously one or two, carbon atoms have been each replaced with a heteroatom, such as sulphur, nitrogen or oxygen atoms. It can be notably a 1,3-dioxolanyl, 1,4-dioxanyl, tetrahydrofuranyl, piperidinyl, pyrrolidinyl or tetrahydropyranyl group, preferably a 1,3-dioxolanyl or 1,4-dioxanyl group.

The term "heteroaryl" as used in the present invention refers to an aromatic heterocycle as defined above.

According to a particular embodiment, the heteroaryl is an aromatic hydrocarbon monocycle or bicycle (i.e. comprising two fused rings), each cycle having 5 or 6 members, notably 6 members, and 1 to 4, notably 1 or 2, carbon atoms having each been replaced with a nitrogen or oxygen atom, notably a nitrogen atom.

A heteroaryl can be notably thiophene, furan, pyrrole, imidazole, pyrazole, oxazole, isoxazole, thiazole, isothiazole, triazoles (1,2,3-triazole and 1,2,4-triazole), benzofuran, indole, benzothiophene, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, etc. In particular, the heteroaryl is thiophene, imidazole, benzimidazole, pyrazine or isoquinoline.

The term "halogen", as used in the present invention, refers to a fluorine, bromine, chlorine or iodine atom.

According to a particular embodiment of the present invention, $R_1$ is H or $(C_1-C_3)$alkyl, preferably ethyl.

$R_1$ can also form together with $R_2$ or $R_4$ a heterocycloalkyl, preferably a 1,3-dioxolanyl or 1,4-dioxanyl group.

In the above definitions of $R_1$, the $(C_1-C_6)$alkyl is preferably methyl, ethyl or isopropyl.

In the above definitions of $R_1$, the $(C_3-C_6)$cycloalkyl is preferably cyclopentyl or cyclohexyl.

In a preferred embodiment, $R_3$, $R_5$ and $R_6$ are H. In another embodiment, $R_2$ and $R_3$ are H. In yet another embodiment, $R_2$ to $R_6$ are H.

In a preferred embodiment, $R_7$ to $R_9$ are, independently of one another, H; halo; or a group selected from $(C_1-C_6)$alkyl, heterocycle, aryl, heteroaryl, —$(C_1-C_6)$alkyl-aryl, and —$(C_1-C_6)$alkyl-heterocycle, said group being optionally substituted with one or several groups selected from halo, —$OR_{36}$, —$NR_{37}R_{38}$, —$SR_{39}$, —$S(O)R_{40}$, —$SO_2R_{41}$, —$SO_2NR_{42}R_{43}$, —$OCOR_{44}$, —$NR_{45}COR_{46}$, —$NR_{47}C(O)OR_{48}$, —$CO_2R_{49}$, —$CONR_{50}R_{51}$, —$OCONR_{53}R_{54}$, —$COR_{55}$, nitro (—$NO_2$), cyano (—CN), oxo (=O), and a group selected from aryl, heterocycle and —$(C_1-C_6)$-heterocycle, said group being optionally substituted with one or several $(C_1-C_6)$-alkyl.

In another embodiment, $R_7$ to $R_9$ represent, independently of one another, H; halo; —$OR_{11}$; —$NR_{12}R_{13}$; —$R_{19}C(O)R_{20}$; —$R_{24}OR_{25}$; or a group selected from $(C_1-C_6)$alkyl, heterocycle, aryl, heteroaryl, —$(C_1-C_6)$alkyl-aryl, and —$(C_1-C_6)$alkyl-heterocycle, said group being optionally substituted with one or several groups selected from halo, —$OR_{36}$, —$NR_{37}R_{38}$, —$SR_{39}$, —$S(O)R_{40}$, —$SO_2R_{41}$, —$SO_2NR_{42}R_{43}$, —$OCOR_{44}$, —$NR_{45}COR_{46}$, —$NR_{47}C(O)OR_{48}$, —$CO_2R_{49}$, —$CONR_{50}R_{51}$, —$OCONR_{53}R_{54}$, —$COR_{55}$, nitro (—$NO_2$), cyano (—CN), oxo (=O), —$(C_1-C_6)$alkyl-heterocycle, and an heterocycle group; $R_{11}$ to $R_{55}$ being as defined above.

In another embodiment, $R_7$ to $R_9$ are, independently of one another, H; halo; —$OR_{11}$; —$NR_{12}R_{13}$; —$R_{19}C(O)R_{20}$; —$R_{24}OR_{25}$; or a group selected from $(C_1-C_6)$alkyl, piperidinyl, morpholinyl, pyrrolidinyl, phenyl, benzyl, thiophenyl, benzimidazolyl or imidazolyl, said group being optionally substituted with one or two groups selected from halo, —$OR_{36}$, —$NR_{37}R_{38}$, —$SR_{39}$, —$S(O)R_{40}$, —$SO_2R_{41}$, —$SO_2NR_{42}R_{43}$, —$OCOR_{44}$, —$NR_{45}COR_{46}$, —$NR_{47}C(O)OR_{48}$, —$CO_2R_{49}$, —$CONR_{50}R_{51}$, —$CO_2R_{52}$, —$OCONR_{53}R_{54}$, —$COR_{55}$, nitro (—$NO_2$), cyano (—CN), oxo (=O), —$(C_1-C_6)$alkyl-heterocycle, and an heterocycle group, preferably —$OR_{36}$, —$NR_{37}R_{38}$, —$OCOR_{44}$, —$NR_{45}COR_{46}$, —$NR_{47}C(O)OR_{48}$, —$CO_2R_{49}$, —$CONR_{50}R_{51}$, —$CO_2R_{52}$, —$OCONR_{53}R_{54}$, —$COR_{55}$, —$(C_1-C_6)$alkyl-heterocycle or an heterocycle group, more preferably —$OR_{36}$ or an —$(C_1-C_6)$alkyl-heterocycle group; $R_{11}$ to $R_{55}$ being as defined above.

In a preferred embodiment, $R_7$ to $R_9$ are, independently of one another, H; halo; or a group selected from $(C_1-C_6)$alkyl, piperidinyl, morpholinyl, pyrrolidinyl, phenyl, benzyl, thiophenyl, benzimidazolyl or imidazolyl, said group being optionally substituted with one or two groups selected from halo, —$OR_{36}$, —$NR_{37}R_{38}$, —$SR_{39}$, —$S(O)R_{40}$, —$SO_2R_{41}$, —$SO_2NR_{42}R_{43}$, —$OCOR_{44}$, —$NR_{45}COR_{46}$, —$NR_{47}C(O)OR_{48}$, —$CO_2R_{49}$, —$CONR_{50}R_{51}$, —$CO_2R_{52}$, —$OCONR_{53}R_{54}$, —$COR_{55}$, nitro (—$NO_2$), cyano (—CN), oxo (=O), —$(C_1-C_6)$alkyl-heterocycle, and an heterocycle group, preferably —$OR_{36}$, —$NR_{37}R_{38}$, —$OCOR_{44}$, —$NR_{45}COR_{46}$, —$NR_{47}C(O)OR_{48}$, —$CO_2R_{49}$, —$CONR_{50}R_{51}$, —$CO_2R_{52}$, —$OCONR_{53}R_{54}$, —$COR_{55}$, —$(C_1-C_6)$alkyl-heterocycle or an heterocycle group, more preferably —$OR_{36}$ or an —$(C_1-C_6)$alkyl-heterocycle group; $R_{11}$ to $R_{55}$ being as defined above.

In another preferred embodiment, $R_7$ to $R_9$ are, independently of one another, H, halo, or a phenyl group, said phenyl group being optionally substituted with one or two groups selected from halo, —$OR_{36}$ and —$(C_1-C_6)$alkyl-heterocycle; $R_{36}$ being as defined above; preferably, $R_{36}$ is a $(C_1-C_6)$alkyl group, more preferably a methyl group.

Advantageously, $R_7$ is H, halo or a phenyl group, said phenyl group being optionally substituted with one or two groups selected from halo, —$OR_{36}$ and —$(C_1-C_6)$alkyl-heterocycle, $R_{36}$ being as defined above. More advantageously, $R_7$ is H or halo.

Advantageously, $R_8$ is H; halo; or a group selected from $(C_1-C_6)$alkyl heterocycle, aryl, heteroaryl, —$(C_1-C_6)$alkyl-aryl, and —$(C_1-C_6)$alkyl-heterocycle, said group being optionally substituted with one or several groups selected from halo, —$OR_{36}$, —$NR_{37}R_{38}$, —$SR_{39}$, —$S(O)R_{40}$, —$SO_2R_{41}$, —$SO_2NR_{42}R_{43}$, —$OCOR_{44}$, —$NR_{45}COR_{46}$, —$NR_{47}C(O)OR_{48}$, —$CO_2R_{49}$, —$CONR_{50}R_{51}$, —$OCONR_{53}R_{54}$, —$COR_{55}$, nitro (—$NO_2$), cyano (—CN), oxo (=O), and a group selected from aryl, heterocycle and —$(C_1-C_6)$alkyl-heterocycle, said group being optionally substituted with one or several $(C_1-C_6)$-alkyl; $R_{11}$ to $R_{55}$ being as defined above.

Advantageously, $R_9$ is H; halo; or a group selected from $(C_1-C_6)$alkyl, aryl and heteroaryl, said group being optionally substituted with one or several groups selected from halo, —$OR_{36}$, —$NR_{37}R_{38}$, —$SR_{39}$, —$S(O)R_{40}$, —$SO_2R_{41}$, —$SO_2NR_{42}R_{43}$, —$OCOR_{44}$, —$NR_{45}COR_{46}$, —$NR_{47}C(O)OR_{48}$, —$CO_2R_{49}$, —$CONR_{50}R_{51}$, —$OCONR_{53}R_{54}$, —$COR_{55}$, nitro (—$NO_2$), cyano (—CN), oxo (=O), and a group selected from aryl, heterocycle and —$(C_1-C_6)$alkyl-heterocycle, said group being optionally substituted with one or several $(C_1-C_6)$-alkyl; $R_{11}$ to $R_{55}$ being as defined above.

More advantageously, $R_8$ and $R_9$ are, independently of one another, H, halo, or a phenyl group, said phenyl group being optionally substituted with one or two groups selected from halo or —$OR_{36}$, $R_{36}$ being as defined above; preferably, $R_{36}$ is a $(C_1-C_6)$alkyl group, more preferably a methyl group.

In a particular embodiment, $R_9$ is H.

In a particular embodiment, $R_8$ and $R_9$ are H and $R_7$ is as defined above.

In another particular embodiment, $R_7$ and $R_9$ are H and $R_8$ is as defined above.

In another particular embodiment $R_7$ to $R_9$ are H.

In the above definitions of $R_7$ to $R_9$, the aryl is preferably a phenyl.

In a preferred embodiment, $R_1$ to $R_{55}$ are, independently of one another, H, halo, or a group selected from $(C_1-C_6)$ alkyl, aryl, heteroaryl, said group being optionally substituted with one or several groups selected from halo, $CF_3$ or methyl.

$R_{12}$-$R_{13}$, $R_{14}$-$R_{15}$, $R_{22}$-$R_{23}$, $R_{34}$-$R_{35}$, $R_{37}$-$R_{38}$, $R_{42}$-$R_{43}$, $R_{50}$-$R_{51}$, and/or $R_{53}$-$R_{54}$ can also form together respectively form a heterocycloalkyl, preferably a 1,3-dioxolanyl, 1,4-dioxanyl, tetrahydrofuranyl, piperidinyl, pyrrolidinyl or tetrahydropyranyl group.

According to a first embodiment:
$R_1$ is H, a $(C_1$-$C_6)$alkyl or a $(C_3$-$C_6)$cycloalkyl or $R_1$ forms together with $R_2$ or $R_4$ a heterocycloalkyl, preferably $R_1$ is H, a $(C_1$-$C_3)$alkyl or $R_1$ forms together with $R_2$ or $R_4$ a heterocycloalkyl;
$R_2$ to $R_6$ are, independently of one another, H or $OR_{10}$;
$R_{10}$ is H or $(C_1$-$C_6)$alkyl;
$R_7$ to $R_9$ are, independently of one another, H; halo; or a group selected from $(C_1$-$C_6)$alkyl, heterocycle, aryl, heteroaryl, —$(C_1$-$C_6)$alkyl-aryl, and —$(C_1$-$C_6)$alkyl-heterocycle, said group being optionally substituted with one or several groups selected from halo, —$OR_{36}$, —$NR_{37}R_{38}$, —$SR_{39}$, —$S(O)R_{40}$, —$SO_2R_{41}$, —$SO_2NR_{42}R_{43}$, —$OCOR_{44}$, —$NR_{45}COR_{46}$, —$NR_{47}C(O)OR_{48}$, —$CO_2R_{49}$, —$CONR_{50}R_{51}$, —$OCONR_{53}R_{54}$, —$COR_{55}$, nitro (—$NO_2$), cyano (—CN), oxo (=O), and a group selected from aryl, heterocycle and —$(C_1$-$C_6)$alkyl-heterocycle, said group being optionally substituted with one or several $(C_1$-$C_6)$-alkyl; and
$R_{36}$ to $R_{55}$ are, independently of one another, H, halo, benzoylbenzyl, or a group selected from $(C_1$-$C_6)$alkyl, aryl, heteroaryl, heterocycle, —$(C_1$-$C_6)$alkyl-heterocycle, and —$(C_1$-$C_6)$alkyl-aryl, said group being optionally substituted with one or several groups selected from halo, $CF_3$ or $(C_1$-$C_6)$alkyl; or $R_{37}$-$R_{38}$, $R_{42}$-$R_{43}$, $R_{50}$-$R_{51}$, and/or $R_{53}$-$R_{54}$ may together respectively form a heterocycloalkyl.

According to a second embodiment of the present invention, in the general formula (I) or a pharmaceutically acceptable salt and/or solvate thereof:
$R_1$ is H and a $(C_1$-$C_6)$alkyl or $R_1$ forms together with $R_2$ or $R_4$ a heterocycloalkyl;
$R_2$ to $R_6$ are, independently of one another, H or $OR_{10}$;
$R_{10}$ is H or $(C_1$-$C_6)$alkyl;
$R_7$ to $R_9$ are, independently of one another H, halo, —$OR_{11}$, —$NR_{12}R_{13}$; —$R_{19}C(O)R_{20}$; —$R_{24}OR_{25}$; or a group selected from $(C_1$-$C_6)$alkyl, piperidinyl, morpholinyl, pyrrolidinyl, phenyl, benzyl, thiophenyl, benzimidazolyl or imidazolyl, said group being optionally substituted with one or two groups selected from halo, —$OR_{36}$, —$NR_{37}R_{38}$, —$SR_{39}$, —$S(O)R_{40}$, —$SO_2R_{41}$, —$SO_2NR_{42}R_{43}$, —$OCOR_{44}$, —$NR_{45}COR_{46}$, —$NR_{47}C(O)OR_{48}$, —$CO_2R_{49}$, —$CONR_{50}R_{51}$, —$OCONR_{53}R_{54}$, —$COR_{55}$, nitro (—$NO_2$), cyano (—CN), oxo (=O), —$(C_1$-$C_6)$alkyl-heterocycle, and an heterocycle group, preferably —$OR_{36}$, —$NR_{37}R_{38}$, —$OCOR_{44}$, —$NR_{45}COR_{46}$, —$NR_{47}C(O)OR_{48}$, —$CO_2R_{49}$, —$CONR_{50}R_{51}$, —$CO_2R_{52}$, —$OCONR_{53}R_{54}$, —$COR_{55}$, —$(C_1$-$C_6)$alkyl-heterocycle or an heterocycle group, more preferably —$OR_{36}$ or an —$(C_1$-$C_6)$alkyl-heterocycle group; preferably H, halo, or a phenyl group, said phenyl group being optionally substituted with one or two groups selected from halo, —$OR_{36}$ and —$(C_1$-$C_6)$alkyl-heterocycle; and
$R_{11}$ to $R_{55}$ are, independently of one another, H, halo, or a group selected from $(C_1$-$C_6)$alkyl, aryl, heteroaryl, said group being optionally substituted with one or several groups selected from halo, $CF_3$ or methyl.

According to a third embodiment of the present invention:
$R_1$ is H, a $(C_1$-$C_3)$alkyl or $R_1$ forms together with $R_2$ or $R_4$ a heterocycloalkyl;
$R_3$, $R_5$ and $R_6$ are H;
$R_2$ and $R_4$ are, independently of one another, H or $OR_{10}$;
$R_{10}$ is H or $(C_1$-$C_6)$alkyl;
$R_7$ to $R_9$ are, independently of one another, H, halo, or a phenyl group, said phenyl group being optionally substituted with one or two groups selected from halo or —$OR_{36}$;
$R_{36}$ is a $(C_1$-$C_6)$alkyl group, more preferably a methyl group.

The compound of general formula (I) can be selected from compounds 1 to 10, preferably 1 to 8, described in the experimental part below and the pharmaceutically acceptable salts and solvates thereof.

According to a particular embodiment of the present invention, in all of the above definitions, the pharmaceutically acceptable salts of the compound of the invention can be the hydrobromic acid addition salts.

According to one particular embodiment, the present invention is directed to the compound of general formula (I) as defined above, for use as inhibitor of cellular necroptosis.

In particular, the present invention is directed to the compound of general formula (I) as defined above, for use for preventing and/or treating disorders associated with cellular necroptosis.

The present invention is also directed to the compound of general formula (I) as defined above, for use for preventing and/or treating disorders associated with tumour-cell-induced endothelial cell necroptosis.

The present invention also relates to a method for inhibiting cellular necroptosis, comprising the administration to a person in need thereof of an effective dose of a compound of formula (I) as defined above. In particular, the present invention relates to a method for preventing and/or treating disorders associated with cellular necroptosis, comprising the administration to a person in need thereof of an effective dose of a compound of formula (I) as defined above. The present invention also relates to a method for preventing and/or treating disorders associated with tumour-cell-induced endothelial cell necroptosis, comprising the administration to a person in need thereof of an effective dose of a compound of formula (I) as defined above.

The present invention also relates to the use of a compound of formula (I) as defined above, for the manufacture of a drug for inhibiting cellular necroptosis. In particular, the present invention also relates to the use of a compound of formula (I) as defined above, for the manufacture of a drug for preventing and/or treating disorders associated with cellular necroptosis. The present invention also relates to the use of a compound of formula (I) as defined above, for the manufacture of a drug for preventing and/or treating disorders associated with tumour-cell-induced endothelial cell necroptosis.

The disorders associated with cellular necroptosis may be particularly trauma, hepatitis, ischemia reperfusion injury such as myocardial infarction and stroke, acute pancreatitis and acute tubular necrosis.

The disorders associated with cellular necroptosis can also be trauma in brain, hepatitis, alcoholic and non-alcoholic steatohepatitis, acute pancreatitis and acute tubular necrosis, heart or kidney transplantation, atherosclerosis, bone marrow failure, viral infection, Crohn's and ulcerative colitis, terminal ileitis, chronic obstructive pulmonary disease or ischemia reperfusion injury such as myocardial infarction or stroke.

The disorders associated with tumour-cell-induced endothelial cell necroptosis may be particularly tumour cells extravasation or metastasis.

The present invention also relates to a pharmaceutical composition comprising at least one compound of formula (I) as defined above and at least one pharmaceutically acceptable excipient, for use for inhibiting cellular necroptosis. The present invention also relates to a pharmaceutical composition comprising at least one compound of formula (I) as defined above and at least one pharmaceutically acceptable excipient, for use for inhibiting tumour-cell-induced endothelial cell necroptosis.

The present invention is also directed to a pharmaceutical composition comprising at least one compound of formula (I) as defined above and at least one pharmaceutically acceptable excipient, for use for preventing and/or treating disorders associated with cellular necroptosis. The present invention is also directed to a pharmaceutical composition comprising at least one compound of formula (I) as defined above and at least one pharmaceutically acceptable excipient, for use for preventing and/or treating disorders associated with tumour-cell-induced endothelial cell necroptosis.

The present invention also relates to a method for inhibiting cellular necroptosis, comprising the administration to a person in need thereof of an effective dose of a pharmaceutical composition as defined above. In particular, the present invention relates to a method for preventing and/or treating disorders associated with cellular necroptosis, comprising the administration to a person in need thereof of an effective dose of a pharmaceutical composition as defined above. The present invention also relates to a method for inhibiting tumour-cell-induced endothelial cell necroptosis, comprising the administration to a person in need thereof of an effective dose of a pharmaceutical composition as defined above. In particular, the present invention relates to a method for preventing and/or treating disorders associated with tumour-cell-induced endothelial cell necroptosis, comprising the administration to a person in need thereof of an effective dose of a pharmaceutical composition as defined above.

The present invention also relates to the use of a pharmaceutical composition as defined above, for the manufacture of a drug for inhibiting cellular necroptosis. In particular, the present invention also relates to the use of a pharmaceutical composition as defined above, for the manufacture of a drug for preventing and/or treating disorders associated with cellular necroptosis. The present invention also relates to the use of a pharmaceutical composition as defined above, for the manufacture of a drug for inhibiting tumour-cell-induced endothelial cell necroptosis. In particular, the present invention also relates to the use of a pharmaceutical composition as defined above, for the manufacture of a drug for preventing and/or treating disorders associated with tumour-cell-induced endothelial cell necroptosis.

The disorders associated with cellular necroptosis may be particularly trauma, hepatitis, ischemia reperfusion injury such as myocardial infarction and stroke, acute pancreatitis and acute tubular necrosis.

The disorders associated with cellular necroptosis can also be trauma in brain, hepatitis, alcoholic and non-alcoholic steatohepatitis, acute pancreatitis and acute tubular necrosis, heart or kidney transplantation, atherosclerosis, bone marrow failure, viral infection, Crohn's and ulcerative colitis, terminal ileitis, chronic obstructive pulmonary disease or ischemia reperfusion injury such as myocardial infarction or stroke.

The disorders associated with tumour-cell-induced endothelial cell necroptosis may be particularly tumour cells extravasation or metastasis.

The pharmaceutical compositions according to the invention may be formulated notably for oral administration or for injection, wherein said compositions are intended for mammals, including humans.

The pharmaceutical composition can be administered orally by means of tablets and gelatin capsules.

When a solid composition is prepared in the form of tablets, the main active ingredient is mixed with a pharmaceutical vehicle such as gelatin, starch, lactose, magnesium stearate, talc, gum arabic and the like. The tablets may be coated with sucrose or with other suitable materials, or they may be treated in such a way that they have a prolonged or delayed activity and they continuously release a predetermined amount of active principle.

A preparation in gelatin capsules is obtained by mixing the active ingredient with a diluent and pouring the mixture obtained into soft or hard gelatin capsules.

For administration by injection, aqueous suspensions, isotonic saline solutions or sterile and injectable solutions which contain pharmacologically compatible dispersing agents and/or wetting agents are used.

The active ingredient may be administered in unit dosage forms of administration, in mixture with standard pharmaceutical carriers, to animals or to humans. The compounds of the invention as active ingredients may be used in doses ranging between 0.01 mg and 1000 mg per day, given in a single dose once per day or administered in several doses throughout the day, for example twice a day in equal doses. The dose administered per day advantageously is between 5 mg and 500 mg, even more advantageously between 10 mg and 200 mg. It may be necessary to use doses outside these ranges as determined by the person skilled in the art.

The pharmaceutical compositions according to the invention may further comprise at least one other active ingredient, such as another cellular necroptosis inhibitor; or an apoptosis inhibitor, an autophagy inhibitor, a ferroptosis inhibitor, an inhibitor of MPT (The mitochondrial permeability transition) pore-dependent necrosis, a cyclophylin inhibitor, a Cyclin-dependent kinase 5 (CDK5) inhibitor, a parthanatos inhibitor, a thrombin inhibitor, an antioxidant (such as glutathione or allopurinol) or an inflammatory inhibitor.

The present invention relates also to a pharmaceutical composition comprising:
(i) at least one compound of formula (I) as defined above, and
(ii) at least one other active ingredient, such as another cellular necroptosis inhibitor; or an apoptosis inhibitor, an autophagy inhibitor, a ferroptosis inhibitor, an inhibitor of MPT (The mitochondrial permeability transition) pore-dependent necrosis, a Cyclin-dependent kinase 5 (CDK5) inhibitor, a parthanatos inhibitor, a thrombin inhibitor, an antioxidant (such as glutathione or allopurinol) or an inflammatory inhibitor,
as a combination product for simultaneous, separate or sequential use.

The present invention also relates to the use of a compound of general formula (I) as defined above; for the preservation and/or protection of biological materials such as cells, tissues, body fluids and organs, and of microorganisms, advantageously as a medical device.

In the context of the present invention, a medical device refers to any product which is put in contact with organs, tissues, cells or products from the human or animal body origin during their conservation, their preparation, their transformation, their packaging or their transport prior to their therapeutic use in humans. A medical device according to the present invention can also be any product coming into contact with embryos in the context of an activity of medically assisted procreation. In particular, this category of products includes graft preservation media (tissues, organs), the media used in the context of in vitro fertilization, or media used during the preparation of cell therapy products.

In particular, the present invention is directed to the use of a compound of general formula (I) as defined above, for use in medium for preserving organs, biological tissue, or living cells, preferably for preserving organs such as for example liver or kidney.

The compound of the invention can thus be used in the case of a graft as a supplementary therapeutic product for preserving cells, tissues or organs between the sampling on a donor and the graft on a receiver.

The examples which follow illustrate the invention without limiting its scope in any way.

BRIEF SUMMARY OF THE FIGURES

FIG. 14 represents the inhibitory effect of Sib (compound 2) in a model of necroptosis-dependent acute hepatitis induced by Concanavalin A (ConA) in mice. The beneficial effects of Sib in vivo are reported in this figure.

EXAMPLES

Figure 1:
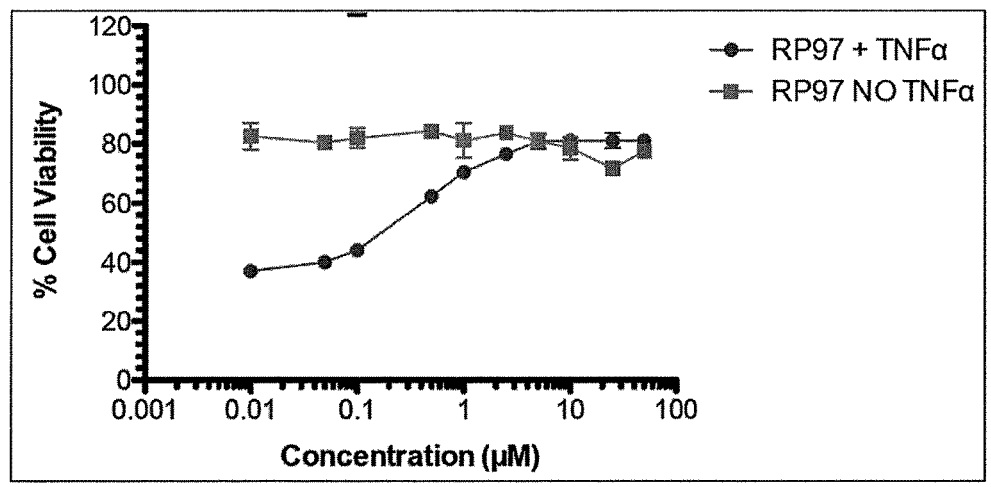
FIG. 1 represents the dose-dependent inhibition by compound 1 of necroptosis induced by TNF-α in human T lymphocyte (Jurkat FADD deficient cell line)
Figure 2:
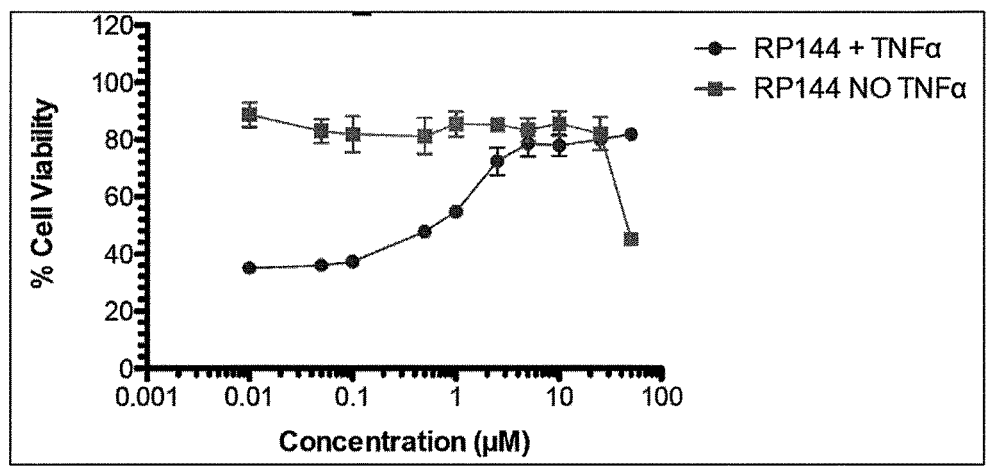
FIG. 2 represents the dose-dependent inhibition by compound 2 (Sibiriline) of necroptosis induced by TNF-α in human T lymphocyte (Jurkat FADD deficient cell line)
Figure 3:
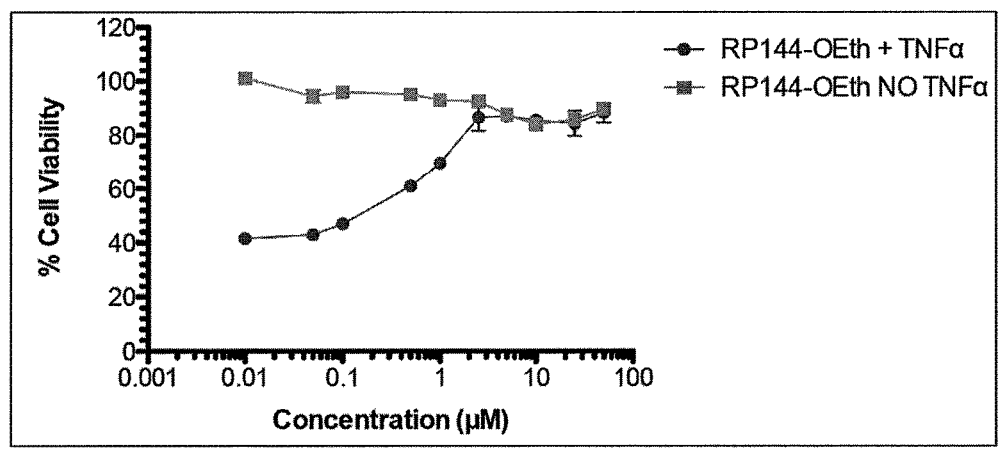
FIG. 3 represents the dose-dependent inhibition by compound 3 of necroptosis induced by TNF-α in human T lymphocyte (Jurkat FADD deficient cell line)
Figure 4:
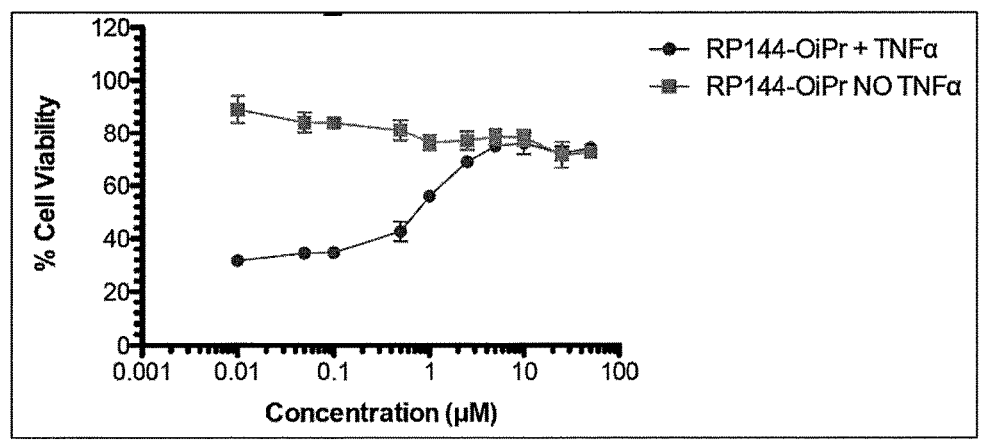
FIG. 4 represents the dose-dependent inhibition by compound 4 of necroptosis induced by TNF-α in human T lymphocyte (Jurkat FADD deficient cell line)
Figure 5:
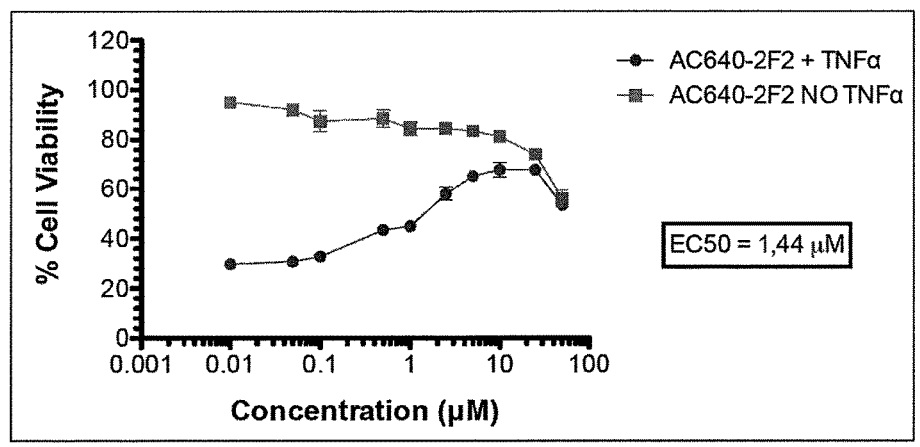
FIG. 5 the dose-dependent inhibition by compound 5 of necroptosis induced by TNF-α in human T lymphocyte (Jurkat FADD deficient cell line)
Figure 6:
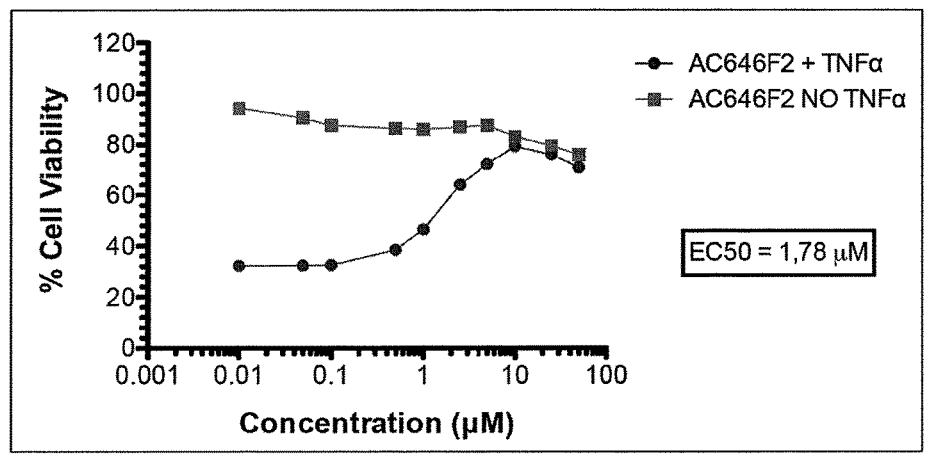
FIG. 6 represents the dose-dependent inhibition by compound 6 of necroptosis induced by TNF-α in human T lymphocyte (Jurkat FADD deficient cell line)
Figure 7:
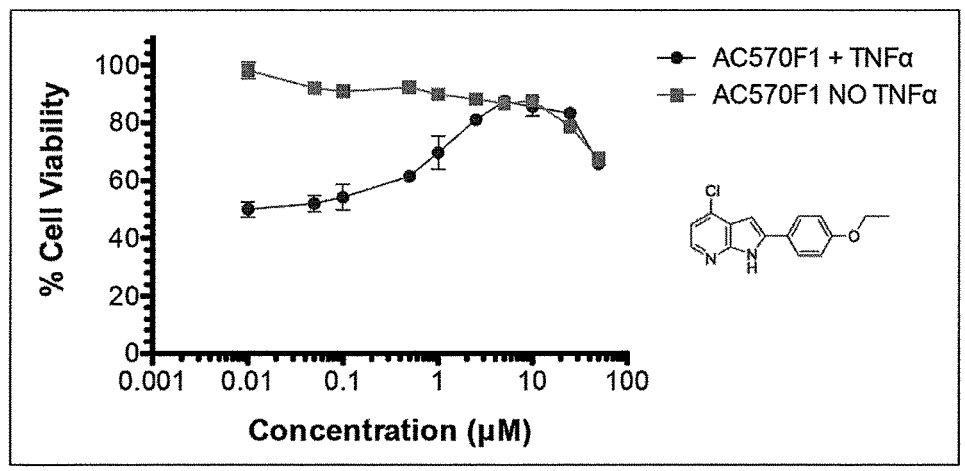
FIG. 7 represents the dose-dependent inhibition by compound 7 of necroptosis induced by TNF-α in human T lymphocyte (Jurkat FADD deficient cell line)
Figure 8:
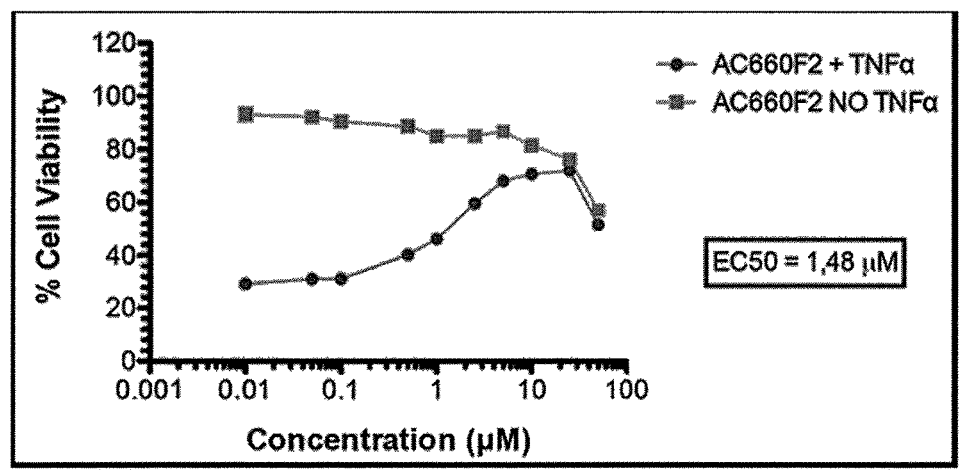
FIG. 8 represents the dose-dependent inhibition by compound 8 of necroptosis induced by TNF-α in human T lymphocyte (Jurkat FADD deficient cell line)

The following abbreviations have been used in the following examples:
ALT: alanine aminotransferase
AST: aspartate aminotransferase
bs: broad singlet
BSA: Bovine Serum Albumin
d: doublet
DMF: Dimethylformamide
DMSO: Dimethylsulfoxyde
DTT: Dithiothreitol
$EC_{50}$: Half maximal effective concentration
EDTA: Ethylenediaminetetraacetic acid
EGTA: Ethylene glycol-bis(β-aminoethyl ether)-N,N,N',N'-tetraacetic acid
eq: equivalent
Et: Ethyl ($CH_2CH_3$)
EtOAc: Ethyl acetate
h: hour
$^1$H-: Protium
Hz: Hertz
$IC_{50}$: Half maximal inhibitory concentration
J: Coupling constant
kg: kilogram
LDA: Lithium diisopropylamide
m: multiplet
M: Molar
mCPBA: Meta-Chloroperoxybenzoic acid
Me: Methyl ($CH_3$)
mg: milligram
MHz: MegaHertz
min: minute(s)
ml: milliliter
mM: Millimolar
mmol: millimole
MOPS: 3-(N-morpholino)propanesulfonic acid
MsCl: Methanesulfonyl chloride
ND: Not determined
nBuLi: n-Butyllithium
NMR: Nuclear Magnetic Resonance
PE: petroleum ether
q: Quadruplet
r.t: Room temperature
sS: Simplet
Sib: Sibiriline
t: Triplet
THF: Tetrahydrofuran
XPhos: 2-Dicyclohexylphosphino-2',4',6'-triisopropylbiphenyl
μg: microgram
μl: Microliter
μM: Micromolar

I. Synthesis of the Compounds According to the Invention

Example 1: Synthesis of O-Substituted Sibs

Synthesis of 2-(4-methoxyphenyl)-1H-pyrrolo[2,3-b]pyridine (compound 1)

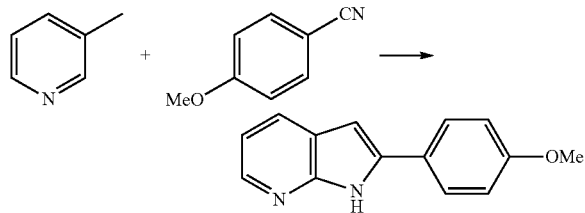

LDA was freshly prepared by adding dropwise a nBuLi solution in hexane (1.5 ml, 2.5 M, 3.9 mmol) under argon to a diisopropylamine (0.54 ml, 3.9 mmol) solution in anhydrous THF (10 ml) at −5° C. and stirring for 20 min. Then a solution of 3-picoline (200 mg, 2.2 mmol, 1 eq) in anhydrous THF (10 ml) was added dropwise at 0° C. and the orange mixture was stirred for 20 min before dropwise addition of a solution of 4-methoxybenzonitrile (316 mg, 2.2 mmol, 1 eq) in anhydrous THF (10 ml). After 1 h at 0° C., more LDA solution in THF (10 ml) was added dropwise (3.9 mmol, prepared from 1.5 ml nBuLi and 0.54 ml diisopropylamine) and the reaction was slowly warmed to r.t during 1 h before being heated to reflux in a water bath for 2 h. After cooling, the yellow solution was quenched carefully with saturated NH$_4$Cl (10 ml) and water (40 ml) was added. The precipitate was filtered, washed with diethyl ether and water, dried under vacuum to afford a light yellow solid (327 mg, 68%).

$^1$H-NMR (300 MHz, CDCl$_3$): 3.89 (s, 3H), 6.70 (s, 1H), 7.04 (d, J=8.8 Hz, 2H), 7.14 (dd, J=7.8, 5.1 Hz, 1H), 7.82 (d, J=8.8 Hz, 2H), 8.00 (dd, J=7.8, 1.3 Hz, 1H), 8.23 (dd, J=5.1, 1.3 Hz, 1H), 12.52 (bs, 1H).

Synthesis of 4-(1H-pyrrolo[2,3-b]pyridin-2-yl)phenol (compound 2)

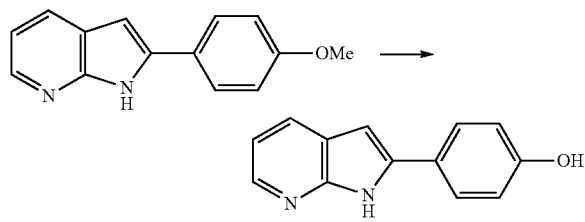

2-(4-methoxyphenyl)-1H-pyrrolo[2,3-b]pyridine (100 mg, 0.44 mmol) was suspended in anhydrous CH$_2$Cl$_2$ (10 ml) and cooled to −78° C. Boron tribromide (1M solution in CH$_2$Cl$_2$, 0.67 mmol, 1.5 eq) was added dropwise and the dark brown mixture was stirred 16 h while slowly warming to r.t. The reaction was carefully quenched with saturated NaHCO$_3$ solution (10 ml) and the aqueous phase was extracted with CH$_2$Cl$_2$ (2×20 ml). The organic extract were washed with brine, dried over MgSO$_4$, filtered and concentrated. The crude product was purified by flash chromatography (95:5 CH$_2$Cl$_2$:MeOH) to afford a light brown solid (61 mg, 65%).

$^1$H-NMR (300 MHz, CDCl$_3$): 6.70 (d, J=2.0 Hz, 1H), 6.85 (d, J=8.7 Hz, 2H), 7.02 (dd, J=7.8, 4.7 Hz, 1H), 7.76 (d, J=8.7 Hz, 2H), 7.85 (dd, J=7.8, 1.3 Hz, 1H), 8.14 (dd, J=4.7, 1.3 Hz, 1H), 9.71 (bs, 1H), 11.93 (bs, 1H).

Synthesis of 2-(4-ethoxyphenyl)-1H-pyrrolo[2,3-b]pyridine (compound 3)

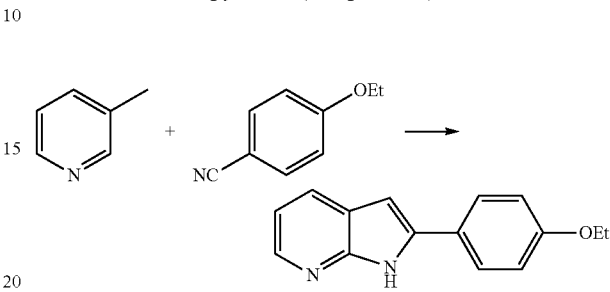

LDA was freshly prepared by adding dropwise a nBuLi solution in hexane (54 ml, 2.5 M, 135 mmol) under argon to a diisopropylamine (19 ml, 135 mmol) solution in anhydrous THF (150 ml) at −5° C. and stirring for 20 min. Then a solution of 3-picoline (7 g, 75 mmol, 1 eq) in anhydrous THF (100 ml) was added dropwise at 0° C. and the orange mixture was stirred for 20 min before dropwise addition of a solution of 4-ethoxybenzonitrile (11.1 g, 75 mmol, 1 eq) in anhydrous THF (100 ml). After 1 h at 0° C., more LDA solution in THF (150 ml) was added dropwise (135 mmol, prepared from 54 ml nBuLi and 19 ml diisopropylamine) and the reaction was slowly warmed to r.t during 1 h before being heated to reflux in a water bath for 2 h. After cooling, the yellow solution was quenched carefully with saturated NH$_4$Cl (100 ml) and water (250 ml) was added. The precipitate was filtered, washed with diethyl ether and water, dried under vacuum to afford a light yellow solid (11 g, 61%).

$^1$H-NMR (300 MHz, DMSO-d$_6$): 1.35 (t, J=7.1 Hz, 3H), 4.07 (q, J=7.1 Hz, 2H), 6.78 (d, J=2.2 Hz, 1H), 7.00-7.05 (m, 3H), 7.85-7.89 (m, 3H), 8.15 (dd, J=4.7, 1.6 Hz, 1H), 12.0 (bs, 1H).

General procedure for O-alkylation of 4-(1H-pyrrolo[2,3-b]pyridin-2-yl)phenol 4-(1H-pyrrolo[2,3-b]pyridin-2-yl)phenol (50 mg, 0.23 mmol) was dissolved in anhydrous DMF (2 ml) under argon, treated with K$_2$CO$_3$ (164 mg, 5 eq, 1.2 mmol) and stirred at r.t. for 15 min before adding the corresponding alkyl iodide or alkyl bromide (3 eq, 0.69 mmol). The mixture was stirred 16 h at the indicated temperature, quenched with water and extracted with EtOAc (2×10 ml). The organic layer was washed with brine, dried over MgSO$_4$, filtered and concentrated. The crude product was purified by flash chromatography (80:20 PE:EtOAc) to afford the desired O-alkylated compounds.

Synthesis of 2-(4-isopropoxyphenyl)-1H-pyrrolo[2,3-b]pyridine (compound 4)

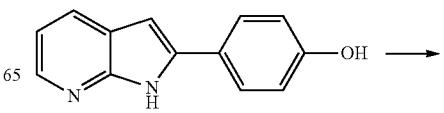

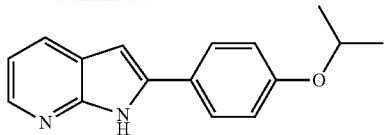

Following the general procedure with isopropyl bromide, stirring at r.t. (32 mg, 55%). $^1$H-NMR (300 MHz, acetone-$d_6$): 1.33 (d, J=6.0 Hz, 6H), 4.67-4.75 (m, 1H), 6.76 (s, 1H), 7.01-7.05 (m, 3H), 7.86-7.89 (m, 3H), 8.16 (d, J=4.6 Hz, 1H), 11.10 (bs, 1H).

Synthesis of 2-(4-(cyclopentyloxy)phenyl)-1H-pyrrolo[2,3-b]pyridine (compound 9)

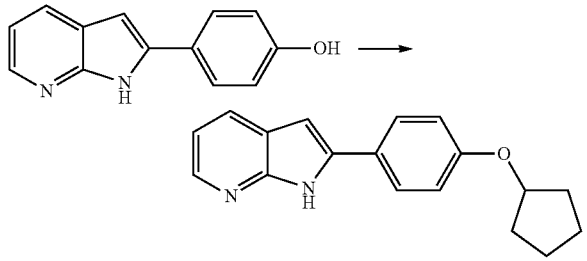

Following the general procedure with cyclopentyl iodide, stirring at 70° C. (12 mg, 20%). $^1$H-NMR (300 MHz, CDCl$_3$): 1.65 (m, 2H), 1.89 (m, 6H), 4.81-4.86 (m, 1H), 6.71 (s, 1H), 6.96-7.03 (m, 2H), 7.16 (dd, J=7.8, 5.2 Hz, 1H), 7.72-7.82 (m, 2H), 8.03 (d, J=7.8 Hz, 1H), 8.20 (d, J=5.1 Hz, 1H), 11.89 (bs, 1H).

Synthesis of tert-butyl 2-(trimethylstannyl)-1H-pyrrolo[2,3-b]pyridine-1-carboxylate

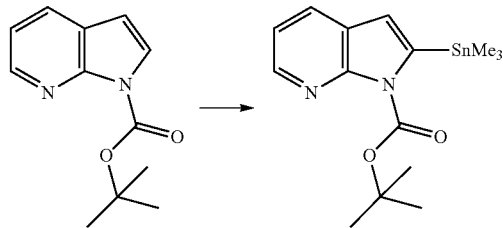

Tert-butyl 1H-pyrrolo[2,3-b]pyridine-1-carboxylate (2 g, 9.17 mmol) was dissolved in anhydrous THF (30 ml) and cooled to −78° C. nBuLi (4 ml, 2.5M, 10 mmol) was added dropwise and the mixture was stirred for 30 min before addition of a solution of trimethyltin chloride (2.18 g, 1.2 eq, 11 mmol) in THF (20 ml). The mixture was stirred 12 h while warming to 0° C. and was carefully quenched with water (100 ml). Extraction with CH$_2$Cl$_2$ (3×50 ml) was performed and the organic extracts were washed with brine, dried over MgSO$_4$, filtered and concentrated. The crude product was purified by flash chromatography (90:10 PE:EtOAc) to afford a colorless oil (3.35 g, 72%). $^1$H-NMR (300 MHz, CDCl$_3$): 0.34 (s, 9H), 1.72 (s, 9H), 6.67 (s, 1H), 7.11 (dd, J=7.8, 4.8 Hz, 1H), 7.78 (dd, J=7.8, 1.7 Hz, 1H), 8.37 (dd, J=4.8, 1.7 Hz, 1H).

Synthesis of 2-(1,4-benzodioxanyl)-1H-pyrrolo[2,3-b]pyridine (compound 5)

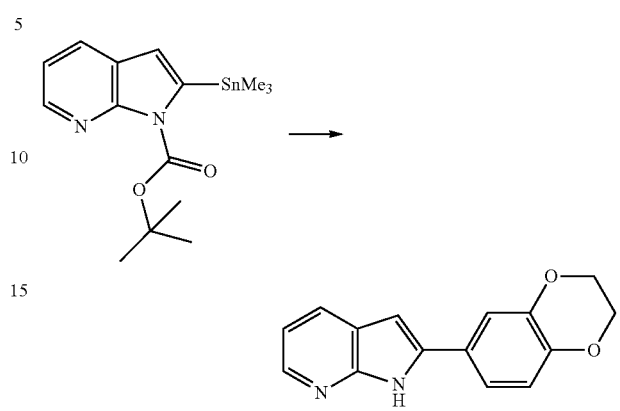

tert-butyl 2-(trimethylstannyl)-1H-pyrrolo[2,3-b]pyridine-1-carboxylate (200 mg, 0.52 mmol) was placed under argon with 6-bromo-2,3-dihydrobenzo[b][1,4]dioxine (135 mg, 1.3 eq, 0.52 mmol), Pd(OAc)$_2$ (11 mg, 0.1 eq, 0.05 mmol) and XPhos (74 mg, 0.3 eq, 0.15 mmol). Anhydrous dioxane (4 ml) was added and the reaction was stirred for 16 h at 100° C. before addition of more Pd(OAc)$_2$ (11 mg) and XPhos (74 mg). Heating was continued for 16 h before cooling to r.t. and adding water (10 ml) and EtOAc (10 ml) to the mixture. The organic phase was extracted with EtOAc (2×10 ml) and the organic extracts were washed with brine, dried over MgSO$_4$, filtered and concentrated. The crude product was purified by flash chromatography (CH$_2$Cl$_2$: EtOAc 95:5 to 85:15) to afford the deprotected coupling compound as a yellow solid (40 mg, 30%).

$^1$H-NMR (300 MHz, CDCl$_3$): 4.34 (s, 4H), 6.66 (s, 1H), 7.00 (d, J=8.4 Hz, 1H), 7.09 (dd, J=7.8, 4.9 Hz, 1H), 7.32 (dd, J=8.4, 2.2 Hz, 1H), 7.37 (d, J=2.1 Hz, 1H), 7.92 (dd, J=7.8, 1.5 Hz, 1H), 8.30 (dd, J=4.9, 1.5 Hz, 1H), 11.38 (bs, 1H).

Synthesis of 2-(1,3-benzodioxolanyl)-1H-pyrrolo[2,3-b]pyridine (compound 6)

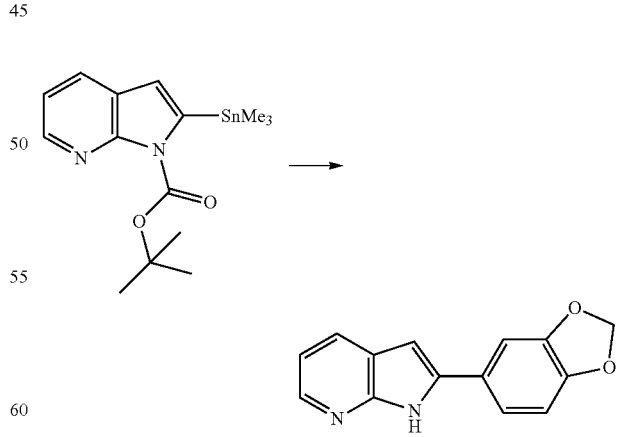

Tert-butyl 2-(trimethylstannyl)-1H-pyrrolo[2,3-b]pyridine-1-carboxylate (200 mg, 0.52 mmol) was placed under argon with 5-bromobenzo[d][1,3]dioxole (81 μL, 1.3 eq, 0.67 mmol), Pd(OAc)$_2$ (11 mg, 0.1 eq, 0.05 mmol) and XPhos (74 mg, 0.3 eq, 0.15 mmol). Anhydrous dioxane (4 ml) was added and the reaction was stirred for 16 h at 100° C. before addition of more Pd(OAc)$_2$ (11 mg) and XPhos (74 mg). Heating was continued for 16 h before cooling to r.t. and adding water (10 ml) and EtOAc (10 ml) to the mixture. The organic phase was extracted with EtOAc (2×10 ml) and the organic extracts were washed with brine, dried over MgSO$_4$, filtered and concentrated. The crude product was purified by flash chromatography (CH$_2$Cl$_2$:EtOAc 95:5 to 85:15) to afford the deprotected coupling compound as a light yellow solid (59 mg, 48%).

$^1$H-NMR (300 MHz, CDCl$_3$): 6.08 (s, 2H), 6.82 (d, J=2.2 Hz, 1H), 7.09-6.98 (m, 2H), 7.47 (dd, J=8.1, 1.6 Hz, 1H), 7.53 (d, J=1.6 Hz, 1H), 7.88 (dd, J=7.8, 1.5 Hz, 1H), 8.17 (dd, J=4.7, 1.5 Hz, 1H), 12.00 (bs, 1H).

Example 2: Synthesis of C4-C6-Substituted Sibs

Synthesis of 2-(4-ethoxyphenyl)-1H-pyrrolo[2,3-b]pyridine-7-oxide

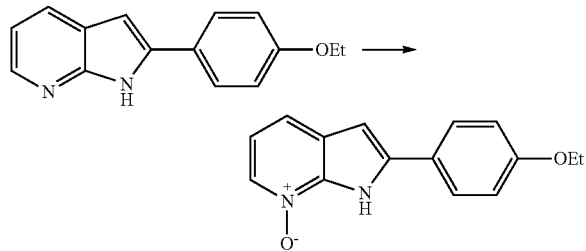

2-(4-ethoxyphenyl)-1H-pyrrolo[2,3-b]pyridine (2 g, 8.4 mmol) was suspended in a mixture of EtOAc (10 ml) and hexane (40 ml) under argon and cooled to 0° C. mCPBA (2.7 g, 12.6 mmol, 1.5 eq) was added in portion, the reaction was slowly warmed to r.t. and stirred for 12 h. The solvent was removed under vacuum and the residue was suspended in saturated K$_2$CO$_3$ solution (50 ml), stirred vigorously for 30 min, filtered and washed with water to obtain a yellow solid that was dried under vacuum (1.5 g, 70%).

$^1$H-NMR (300 MHz, DMSO-d$_6$): 1.35 (t, J=7.1 Hz, 3H), 4.08 (q, J=7.1 Hz, 2H), 6.92 (s, 1H), 6.99-7.09 (m, 3H), 7.56 (d, J=7.1 Hz, 1H), 7.96 (d, J=8.8 Hz, 2H), 8.08 (d, J=6.3 Hz, 1H), 12.7 (bs, 1H).

Synthesis of 4-chloro-2-(4-ethoxyphenyl)-1H-pyrrolo[2,3-b]pyridine (compound 7)

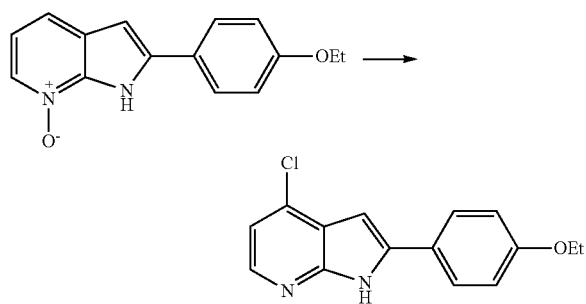

2-(4-ethoxyphenyl)-1H-pyrrolo[2,3-b]pyridine-7-oxide (1 g, 4.1 mmol) was dissolved in anhydrous DMF (10 ml) under argon and MsCl was added dropwise (487 µl, 6.15 mmol, 1.5 eq). The reaction was heated to 80° C. and stirred for 6 h before cooling with an ice bath to yield a precipitate. Water (40 ml) was added and the yellow solid was filtered, washed with more water and dried under vacuum (696 mg, 65%).

$^1$H-NMR (300 MHz, DMSO-d$_6$): 1.35 (t, J=7.0 Hz, 3H), 4.09 (q, J=7.0 Hz, 2H), 6.85 (d, J=2.1 Hz, 1H), 7.02 (d, J=8.8 Hz, 2H), 7.17 (d, J=5.2 Hz, 1H), 7.92 (d, J=8.8 Hz, 2H), 8.12 (d, J=5.2 Hz, 1H), 12.39 (bs, 1H).

Synthesis of 5-bromo-3-((4-ethoxyphenyl)ethynyl)pyridin-2-amine

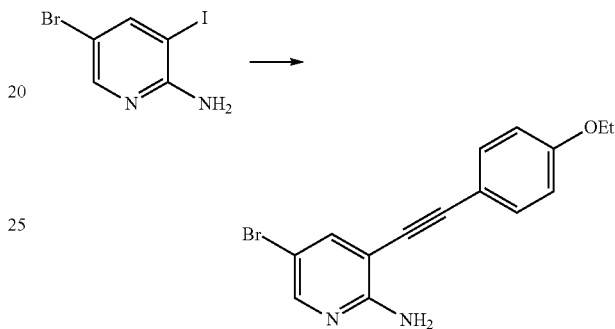

5-bromo-3-iodopyridin-2-amine (5 g, 16.7 mmol) was placed under argon and dissolved in anhydrous THF (50 ml). Et$_3$N (11.5 ml, 5 eq, 83 mmol) and 1-ethoxy-4-ethynylbenzene (2.93 g, 1.2 eq, 20 mmol) were added, followed by CuI (80 mg, 0.025 eq, 0.42 mmol) and PdCl$_2$(PPh$_3$)$_2$ (290 mg, 0.025 eq, 0.42 mmol). The dark brown mixture was stirred at r.t. for 3 h, before water (150 ml) and CH$_2$Cl$_2$ (150 ml) were added. The aqueous layer was extracted with CH$_2$Cl$_2$ and the organic extracts were washed with water and brine, dried over MgSO$_4$ and concentrated. The crude product was purified by flash chromatography (PE:EtOAc gradient 90:10 to 75:25) to afford the desired compound (4.6 g, 87%).

$^1$H-NMR (300 MHz, CDCl$_3$): 1.43 (t, J=7.0 Hz, 3H), 4.06 (q, J=7.0 Hz, 2H), 5.12 (bs, 2H), 6.84-7.03 (m, 2H), 7.38-7.53 (m, 2H), 7.68 (s, 1H), 8.17 (s, 1H).

Synthesis of 5-bromo-2-(4-ethoxyphenyl)-1H-pyrrolo[2,3-b]pyridine (compound 10)

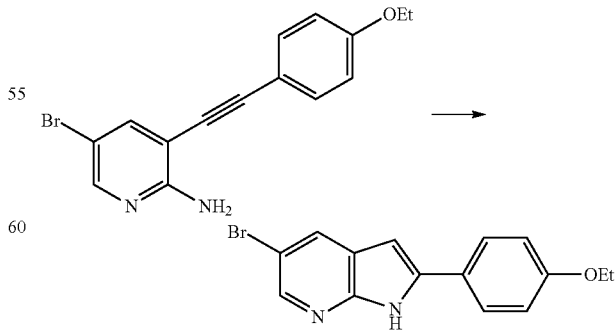

5-bromo-3-((4-ethoxyphenyl)ethynyl)pyridin-2-amine (1 g, 3.34 mmol) was placed under argon in a 5 ml microwave tube and anhydrous DMSO (2 ml) was added, followed by Cs$_2$CO$_3$ (2.17 g, 2 eq, 6.68 mmol). The mixture was stirred at 180° C. for 20 min in a Biotage Initiator microwave reactor. After cooling, the reaction was diluted with water (15 ml), the precipitate was filtered, washed well with water (50 ml) and dried under vacuum to obtain a brown solid, used without further purification (970 mg, 97%).

$^1$H-NMR (300 MHz, DMSO-d$_6$): 1.35 (t, J=7.0 Hz, 3H), 4.08 (q, J=7.0 Hz, 2H), 6.77 (s, 1H), 7.02 (d, J=8.7 Hz, 2H), 7.86 (d, J=8.7 Hz, 2H), 8.10 (d, J=2.2 Hz, 1H), 8.20 (d, J=2.2 Hz, 1H), 12.24 (bs, 1H).

General Procedure for Suzuki Coupling of 5-bromo-2-(4-ethoxyphenyl)-1H-pyrrolo[2,3-b]pyridine 5-bromo-2-(4-ethoxyphenyl)-1H-pyrrolo[2,3-b]pyridine (50 mg, 0.16 mmol) was charged into a vial with Pd(OAc)$_2$ (4 mg, 0.1 eq, 0.016 mmol), SPhos (13 mg, 0.2 eq, 0.031 mmol), K$_2$CO$_3$ (65 mg, 3 eq, 0.47 mmol) and the corresponding boronic acid or boronate ester (1.2 eq, 0.19 mmol). The vial was placed under argon and a mixture of dioxane (1.8 ml) and water (0.2 ml) was added before stirring 16 h at 100° C. After cooling the reaction was diluted with EtOAc and water, extracted with EtOAc (3×10 ml), washed with brine, dried over MgSO$_4$, filtered and concentrated. The crude product was purified by flash chromatography to afford the desired compound.

Synthesis of 5-(3,4-dimethoxyphenyl)-2-(4-ethoxyphenyl)-1H-pyrrolo[2,3-b]pyridine (compound 8)

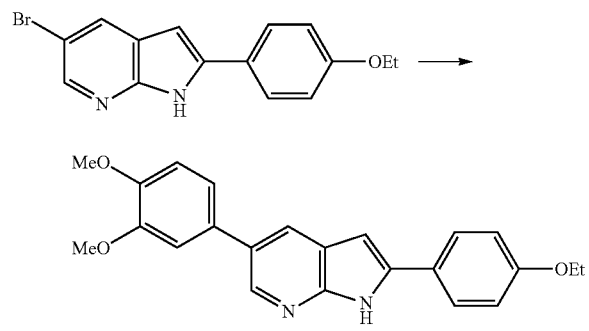

Following the general procedure with 3,4-dimethoxybenzeneboronic acid (28 mg, 47%).

$^1$H-NMR (300 MHz, DMSO-d$_6$): 1.35 (t, J=6.9 Hz, 3H), 3.80 (s, 3H), 3.87 (s, 3H), 4.09 (q, J=7.0 Hz, 2H), 6.82 (d, J=1.9 Hz, 1H), 6.98-7.10 (m, 3H), 7.17-7.32 (m, 2H), 7.88 (d, J=8.8 Hz, 2H), 8.10 (d, J=2.0 Hz, 1H), 8.46 (d, J=2.0 Hz, 1H), 12.06 (bs, 1H).

II. Biological Tests of the Compounds According to the Invention

Example 3: Cell-Based Screening of Chemical Libraries for Characterization of Necroptosis Inhibitors TNF-α can induce necroptosis in Jurkat cells (human T lymphocytes) when FADD is deleted. This model was used to screen various libraries of chemical compounds for characterization of new inhibitors of cellular necroptosis. Details on this cell-based assay can be found in (Miao and Degterev, *Methods Mol. Biol.* 2009, 559, 79-93). The Jurkat FADD-deficient I 2.1 cell line used was purchased from ATCC and was maintained in RPMI 1640 medium (Gibco) containing Glutamax and 15% fetal calf serum (Life Technology). Necroptosis was induced by addition of 10 ng/ml of human recombinant TNF-α (Life Technology). Necrostatin-1 (Nec-1, Enzo Life Sciences) was used as model necroptosis inhibitor. Cells were maintained in 75 cm$^2$ flask and passed every 2 or 3 days. Chemical collections analysed were formatted in 96-well plates with 80 molecules per plates at 10 mM in 100% DMSO. For each collection plate, 2 cell plates were seeded (one necroptosis-induced with TNF-α and the other without TNF-α). Cells were seeded at 20000 cells/well, in 40 µl of medium, in a 96-well clear, flat bottom plate (CytoOne, Starlab) before treatment. Then, 40 µl of medium with or without TNF-α at 25 ng/ml were added to all wells in the corresponding plate. Immediately after TNF-α addition, 20 µl of diluted compound at 50 µM were added to the plates. Final concentration of each chemical compound was 10 µM at 0.1% DMSO. Four positives (Nec-1 at 10 µM final) and four negative (DMSO) controls were used in each plate to validate the assay. Cells were incubated at 37° C., 5% CO$_2$ for 24 hours before performing MTS viability assay, described hereafter. Compounds were diluted before to treat cells. Liquid handling was performed using the Nimbus Microlab liquid handler (Hamilton Robotics) under microbiological safety workbench. The 10 mM compounds were diluted at 50 µM directly in cell medium.

The results of these tests obtained with the compounds of the invention are indicated below and in FIGS. 1 to 8:

| No | Compound | EC$_{50}$ (µM) |
|----|----------|----------------|
| 1  |          | 0.4            |
| 2  |          | 1.3            |
| 3  |          | 0.7            |
| 4  |          | 0.9            |
| 5  |          | 1.4            |

-continued

| No | Compound | EC$_{50}$ (μM) |
|---|---|---|
| 6 | 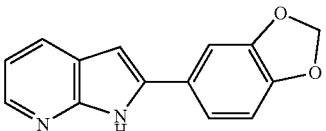 | 1.8 |
| 7 | 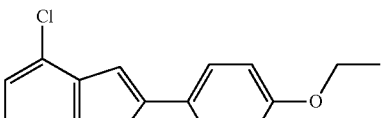 | 2 |
| 8 |  | 1.5 |
| 9 | 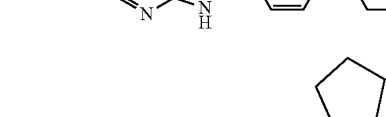 | 3 |

Table 1 below shows the anti-necroptotic effect of Sib using various "death models":

TABLE 1 anti-necroptotic effect of Sib

| Cell Type | Necroptosis Inducer | Average % Cell Death | Sibiriline | |
|---|---|---|---|---|
| | | | EC$_{50}$ | % Rescue |
| L929 | TNF + zVAD | 95% | 3 μM | 80% |
| L929AsFas | FasL + zVAD | 95% | 2.4 μM | 80% |
| Jurkat-Fadd$^{-/-}$ | TNF | 50% | 1.2 μM | 90% |
| U937 | Trail + zVAD | 55% | 4 μM | 90% |
| U937 | Trail + zVAD + CHX | 80% | 20 μM | 50% |

Besides, the IC$_{50}$ of compound 3, compound 6 and necrostatin-1 (Nec-1) were determined in mouse or human cellular models of necroptosis induced by FasL+zVAD-fmk (a pan-caspase inhibitor) or TNF, and by using two cytotoxic assays (MTS Cell Proliferation assay or intracellular ATP level). As shown in the table below, compound 3 and compound 6 inhibit TNF-α or FasL-induced necroptosis with IC$_{50}$ almost similar to those obtained with Nec-1.

TABLE 2 anti-necroptotic effects of compound 3, compound 6 or necrostatin-1 (Nec-1)

| Cell lines Necroptosis inducer | Assays | (compound with OEt) | (compound with dioxole) | Nec-1 |
|---|---|---|---|---|
| L929sAhFas FasL + Zvad | ATP level | 2.5 μM | ND | 10 μM |
| | MTS | ND | 10 μM | 10 μM |
| Jurkat Fadd$^{-/-}$ TNF | ATP level | 1.3 μM | 4 μM | 1.3 μM |
| | MTS | 2.7 μM | 7 μM | 1.3 μM |

Example 4: Anti-Necroptotic Effect of Sib

L929 cells, L929AsFas cells, Jurkat FADD-deficient cells (Jurkat FADD$^{-/-}$), U937 cells are pretreated for 1 h with increased concentrations of Sib (0, 5, 10, 20 μM) and then treated respectively with TNF-α (10 ng/ml)+zVAD (20 μM), FasL (200 ng/ml)+zVAD (20 μM), TNF-α (10 ng/ml), TRAIL (200 ng/ml)+zVAD (30 μM) or TRAIL (200 ng/ml)+zVAD (30 μM)+CHX (1 μg/ml). % of cell death is determined after 24 h and calculated by a FACS analysis of Propidium Iodide-stained nuclei. In each case, the EC50 is determined as well as the % of rescue from cell death.

Example 5: Impact of a Delayed Treatment of Sib on the Necroptotic Cell-Death

Jurkat Fadd deficient cells are treated with TNF-α (10 ng/ml) then treated with Sib (10 μM) at 1 h, 2 h, 3 h or 4 h after adding TNF-α. % of cell death is determined after 24 h and calculated by a FACS analysis of Propidium Iodide-stained nuclei. Quantitative analysis of three independent experiments with means±SD.

Figure 9:
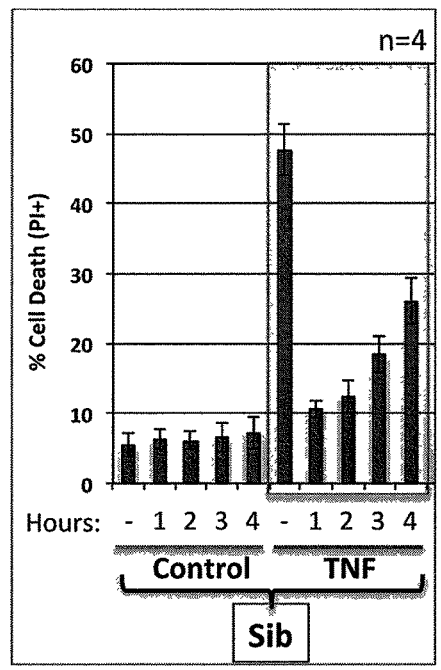
FIG. 9 represents the inhibitory effect of Sibiriline (Sib, compound 2) on TNF-induced necroptosis when Sib was added 1, 2, 3 or 4 hours after the beginning of TNF treatment in Jurkat FADD deficient cells.

The results of these tests are indicated in FIG. 9. Sib inhibits the necroptotic cell-death even if the drug is added after (up to 4 hours) the addition of the death inducer.

Example 6: Clonogenic Assay (CA)

This effect of Sibiriline on necroptosis was verified using clonogenic assay (CA). CA is an in vitro cell survival assay based on the ability of a single cell to grow into a colony.

L929 cells are treated by TNF-α (10 ng/ml)/z-VAD (20 μM) w/or w/o 10 μM Sib for 24 hours. After treatment, cells are seeded out in appropriate dilutions (here 5,000 cells per well) to form colonies in 2 weeks. Colonies are fixed with ice cold methanol and stained with crystal violet.

Figure 10:
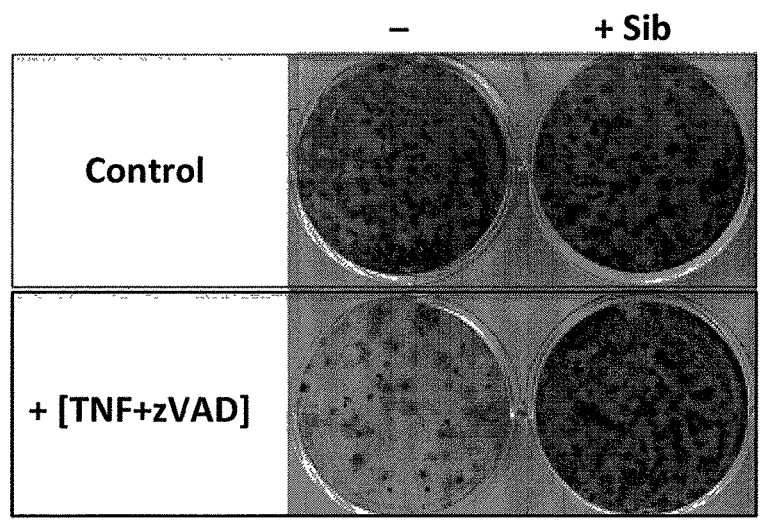
FIG. 10 represents a clonogenic assay showing that Sibiriline (Sib, compound 2) treatment can restore the cellular growth and protect L929 cells from death induced by TNF-α+zVAD.

The results of these tests are indicated in FIG. 10. After 15 days of culture, cell colonies indicate that Sib treatment can restore the cellular growth and protect cells from death induced by TNF-α.

Example 7: RIPK1 Autophosphorylation Assay and Binding Assay

RIPK1 Autophosphorylation Assay:

Human RIPK1 full length GST-tagged was baculovirally expressed in Sf9 cells according to manufacturer's instructions (Bac-to-Bac expression system, Invitrogen) and purified using gluthation-sepharose beads (GE Healthcare). The elution was made in 50 mM Tris-HCl, pH 8.0 buffer supplemented with 30 mM reduced gluthatione (Sigma). The protocol used to detect the enzymatic activity is adapted from Miao and Degterev (*Methods Mol. Biol.* 2009, 559, 79-93). Kinase reaction was initiated mixing 5 μl of eluted RIPK1, 5 μl of 3× kinase reaction buffer (5 mM MOPS pH 7.2, 2.5 mM β-glycerophosphate, 4 mM $MgCl_2$, 2.5 mM $MnCl_2$, 1 mM EGTA, 0.4 mM EDTA, 50 μg/ml BSA, 0.05 mM DTT), 2 μl $H_2O$ and 3 μl of the tested molecule. The mixture was kept on ice for 10 minutes. During the incubation, the ATP solution was prepared by mixing 5 μl of 3× kinase reaction buffer, 4 μl $H_2O$, 6 μl cold ATP at 150 μM and 2 μCi of [$\gamma$-$^{32}$P] ATP. Add the ATP solution and the tested inhibitor to the kinase and incubate for 30 minutes at 30° C. To stop the enzymatic reaction, 5 μl of loading buffer were added and solution was heated for 3 minutes at 95° C. 25 μl of each reaction were loaded per well in pre-cast NuPage 12% Bis-Tris gel (Life Technology). Autophosphorylated RIPK1 band was visualized on radiographic film after 6 h exposition at −80° C.

Figure 11:
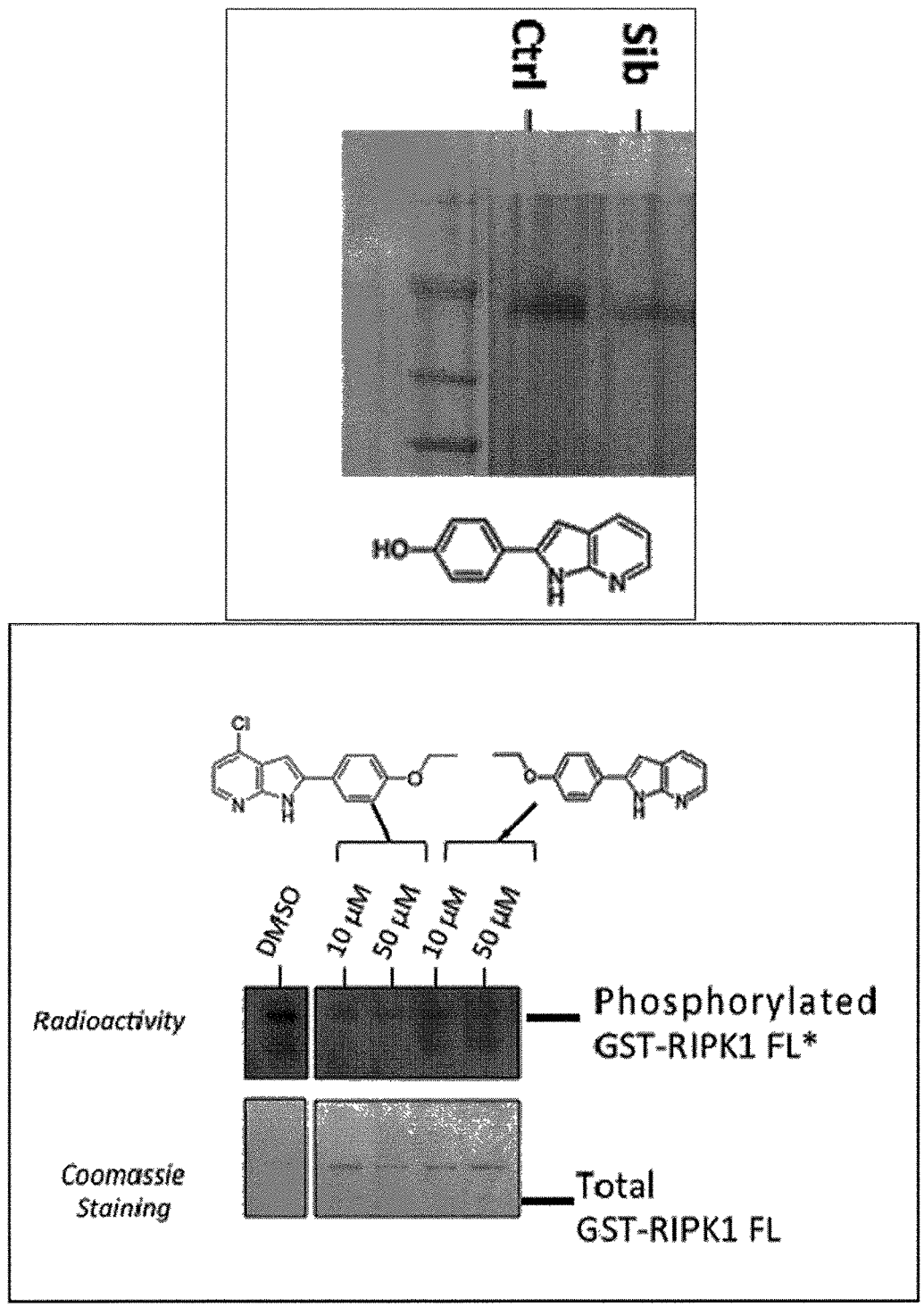
FIG. 11 represents the dose-dependent inhibition of RIPK1 autophosphorylation by compound 2, 3 and 7.

The results of this test obtained with the compounds of the invention are indicated in FIG. 11. The decrease of the amount of radioactively labeled RIPK1 indicates that Sib and its tested derivatives inhibit the RIPK1 autophosphorylation.

Binding Assay for Determination of Binding Constant (Kd) of Sib for RIPK1 Kinase:

KdELECT is a service of DiscoveRx Corporation, Fremont, USA. This assay is based on a competition binding assay that quantitatively measures the ability of a compound to compete with an immobilized, active-site directed ligand. The assay is performed by combining three components: DNA-tagged kinase (here RIPK1); immobilized ligand; and a test compound (here Sib). The ability of Sib to compete with the immobilized ligand is measured via quantitative PCR of the DNA tag. An 11-point 3-fold serial dilution of Sib was prepared in 100% DMSO in order to determine the binding constant (Kd).

Figure 12:
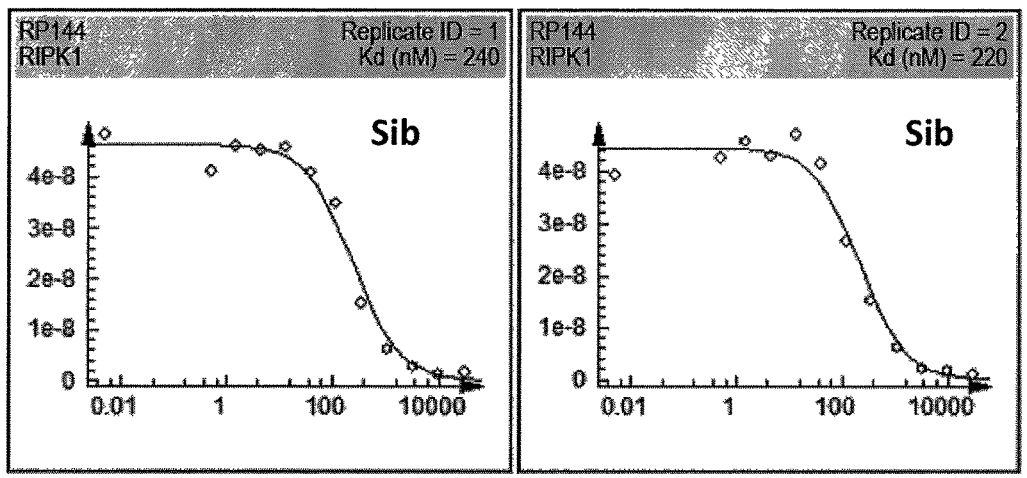
FIG. 12 represents the determination of binding constant (Kd) of Sib (compound 2) for its major cellular target RIPK1.

Kd was then calculated with a standard dose-response curve (reported on FIG. 12) using the Hill equation. The calculated Kd of Sib for RIPK1 is 230±10 nM (n=2). It validates Sib as a true ligand of RIPK1 kinase. As the Kd value is low (nM range), the interaction between RIPK1 and Sib is strong.

Binding Assay for Characterization of Kinase Targets of Sib:

The assay is performed by combining three components: DNA-tagged kinase (a total of 456 kinases were tested); immobilized ligand; and a test compound (here Sib). The ability of Sib to compete with the immobilized ligand is measured via quantitative PCR of the DNA tag. The affinity of Sib for the tested kinase is evaluated by detection of the remaining amount of kinase on the matrix after competition with Sib tested at 10 μM. Nine protein kinases and mutant have been shown to strongly interact with Sib (1% or less of 1% of the amount of the tested kinase is still on the matrix after competition with 10 μM of Sib: JAK2(JH1domain-catalytic), RIPK1, KIT(V559D), EPHB6, AURKC, DRAK2, PDGFRB, KIT and ABL1(H396P)-nonphosphorylated (Table 2). RIPK1, KIT and mutant KIT(V559D), Aurora Kinase C, ABL1(H396P)-nonphosphorylated and PDGFRB were reported to be involved in cancer. ABL1, KIT and PDGFR are targets of already marketed cancer therapeutic drugs. The major kinase targets of Sib are summarized below in table 3.

TABLE 3

| major kinase targets of Sib (compound 2) | | |
|---|---|---|
| Kinase tested | Entrez Gene Symbol | Percent Control (%) |
| JAK2 (JH1domain-catalytic) | JAK2 | 0.2 |
| RIPK1 | RIPK1 | 0.2 |
| KIT(V559D) | KIT | 0.4 |
| EPHB6 | EPHB6 | 0.65 |
| AURKC | AURKC | 0.7 |
| DRAK2 | STK17B | 0.75 |
| PDGFRB | PDGFRB | 0.75 |
| KIT | KIT | 0.8 |
| ABL1(H396P)-nonphosphorylated | ABL1 | 1 |

Example 8: Ethoxyresorufin O-deethylase (EROD) activity

EROD activity corresponds to the O-deethylation of ethoxyresorufin and is mainly supported by cytochrome P450 CYP1A enzymes in HepG2 cells. Induction of CYP1A is mediated through the binding of xenobiotics to a cytosolic aryl hydrocarbon receptor AhR.

Human liver cancer cell lines HepG2 were treated with 10 μM of Sib, Nec-1 or Nec-1s for 24 hours. After treatment, HepG2 cells were incubated in PBS containing 5 mM ethoxyresorufin and kinetic reading was performed at 37° C. with spectrofluorometer (SpectraMax Gemini SX) over a 15 min period.

Figure 13:
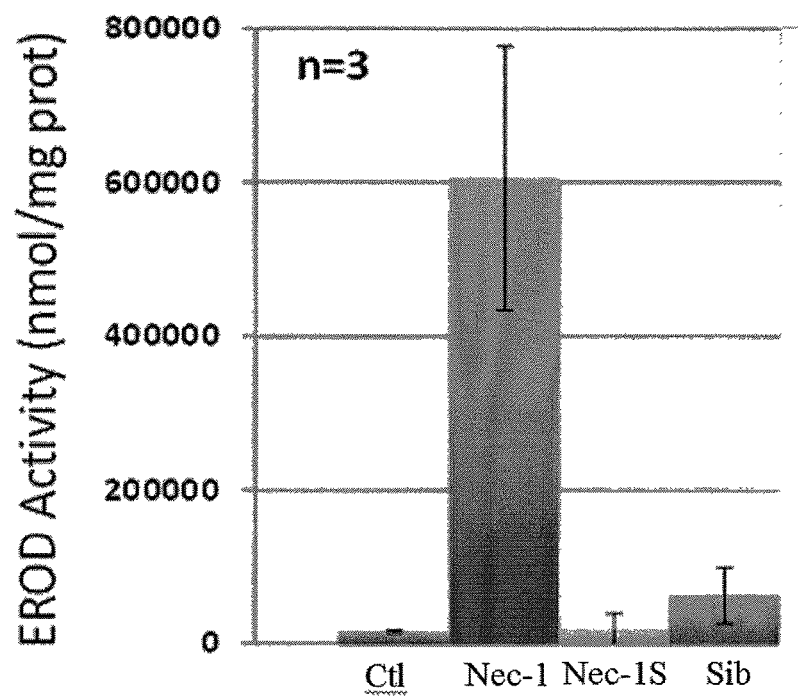
FIG. 13 represents the absence of EROD (Ethoxyresorufin-O-deethylase) activity induced by Sib (compound 2) treatment in HepG2 cells showing that Sib is not a ligand of AhR and does not induce phase I drug metabolism enzymes.

The results of these tests are indicated in FIG. 13. By contrast to Nec-1, Sib or Nec-1s (derivative of Nec-1) at 10 μM do not induce EROD activity (FIG. 11), suggesting that these compounds are not ligands of AhR and do not induce phase I drug metabolism enzymes.

Example 9: In Vivo Effect of Sibirilines

We use a murine model of acute hepatitis (concanavalin A-induced hepatitis) that depends on necroptosis induction (Jouan-Lanhouet et al. *Semin. Cell. Dev. Biol.* 2014, 35, 2-13). Sib is diluted in 50% PBS/50% DMSO.

C57Bl/6 WT mice were pre-treated or not with 3, 6 or 9 mg/kg Sib or 6.25 mg/kg Nec-1s injected by intraperitoneal route 1 hour before treatment or not with 12 mg/kg Con A for 10 h (intravenous route) (50% PBS/50% DMSO, n=5;

50% PBS/50% DMSO+Con A, n=5; 3 mg/kg Sib+Con A, n=5; 6 mg/kg Sib+Con A, n=5; 9 mg/kg Sib+Con A, n=5; 6.25 mg/kg Nec-1s+Con A, n=5).

Figure 14A:
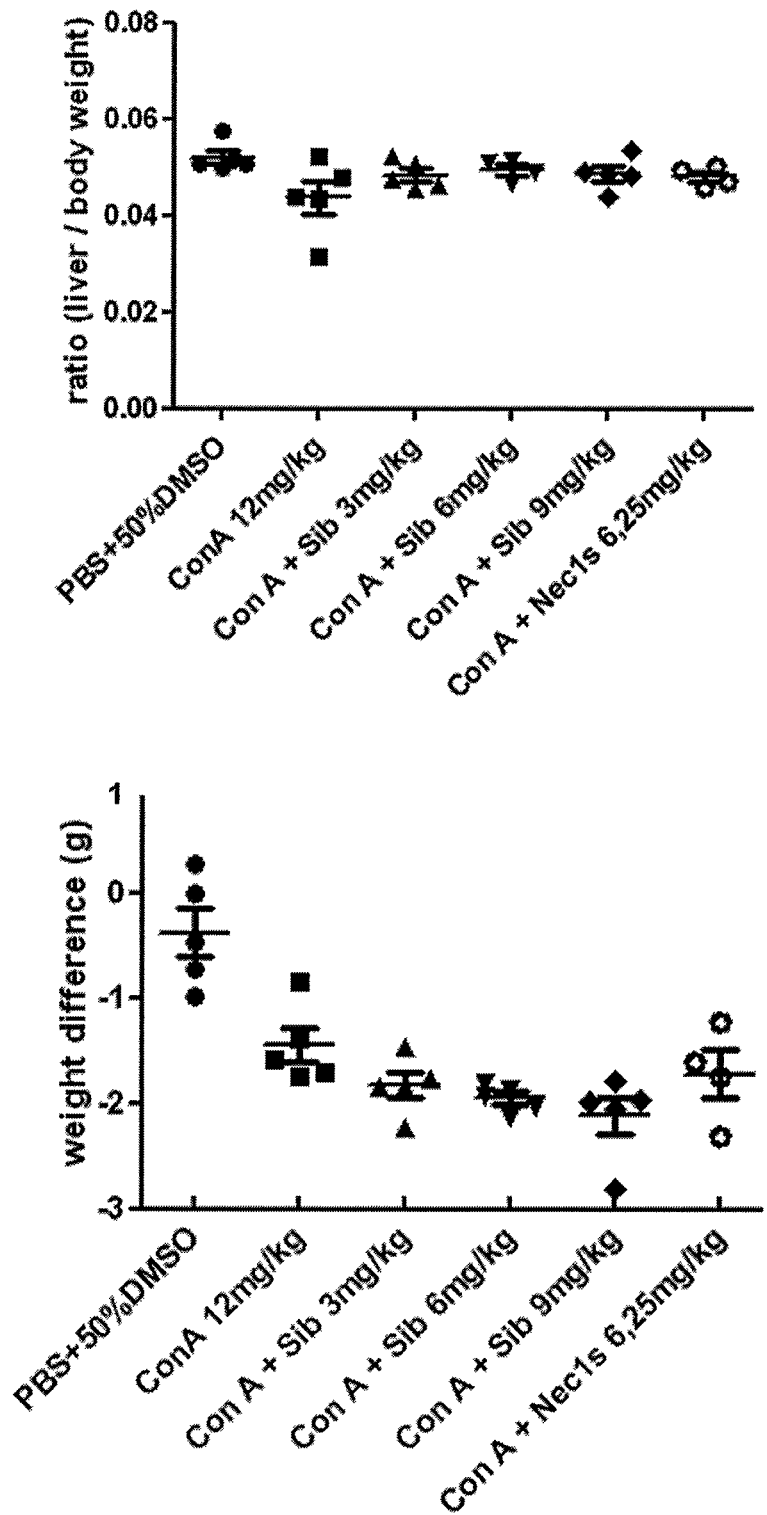
FIG. 14A shows the ratio (liver/body weight) and the weight differences of mice receiving different treatments.
Figure 14B:
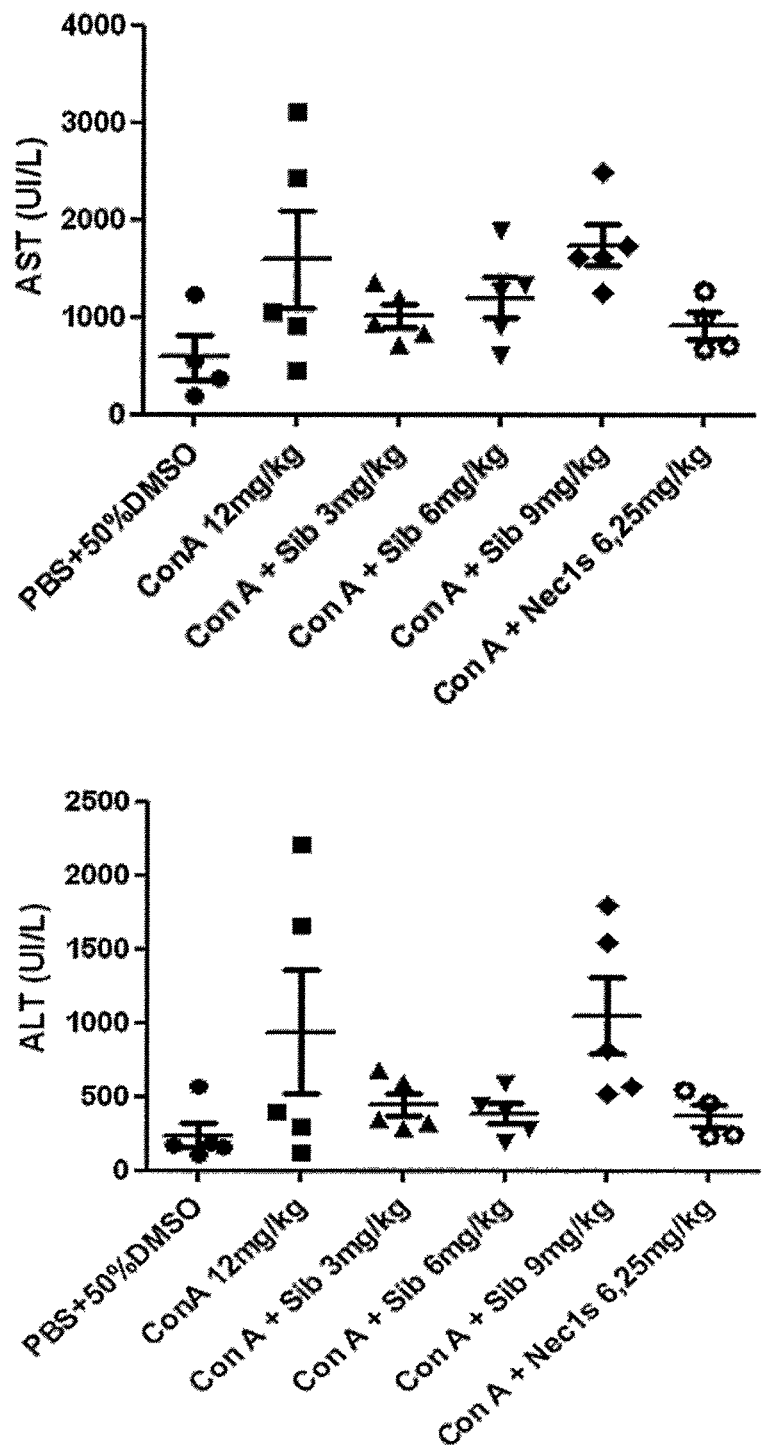
FIG. 14B shows that the serum aminotransaminases (ALT, AST) levels increase when mice receive injection of ConA which is correlated to liver injury. Sib (compound 2) at the dose of 3 mg/kg decreases these serum transaminase levels induced by ConA.
Figure 15:
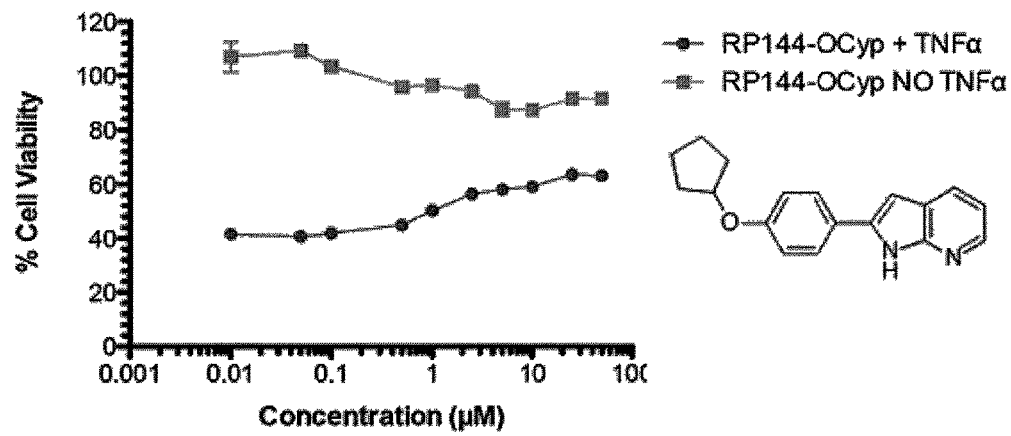
FIG. 15 represents the dose-dependent inhibition by compound 9 of necroptosis induced by TNF-α in human T lymphocyte (Jurkat FADD deficient cell line)
Figure 16:
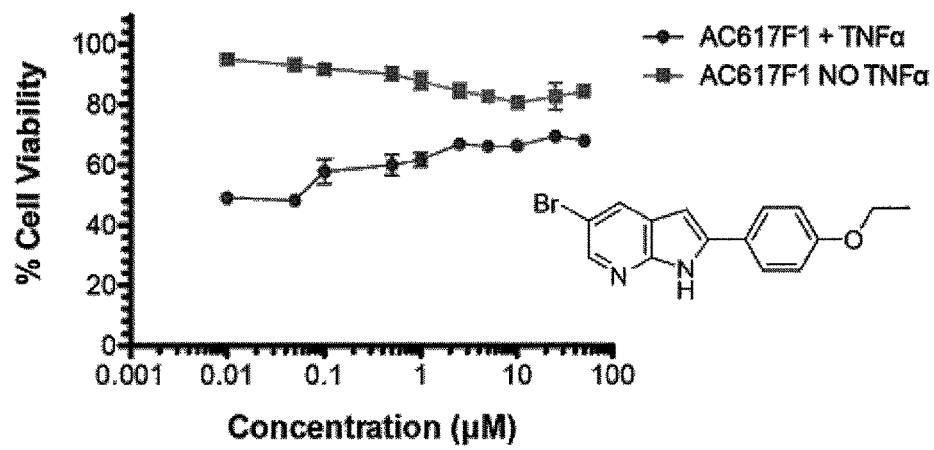
FIG. 16 represents the slight dose-dependent inhibition by compound 10 of necroptosis induced by TNF-α in human T lymphocyte (Jurkat FADD deficient cell line).

Up to 9 mg/kg, Sib has no effect on the ratio (liver/body weight) (FIG. 14A). Treatment with 12 mg/kg concanavalin A for 10 hours increases the serum levels of AST and ALT (FIG. 14B) showing hepatoxicity induced by Con A. Similar to pretreatment with Nec1s at 6.25 mg/kg, pretreatment with Sib at 3 or 6 mg/kg has a tendency to decrease AST and ALT levels and to protect mice from Con A-induced hepatitis. This protection is not observed with Sib used at 9 mg/kg.

Sib at 3 or 6 mg/kg has a tendency to protect mice from con A-induced hepatitis.

The invention claimed is:

1. A method for inhibiting cellular necroptosis comprising the administration to a patient in need thereof of an effective amount of a compound of the following general formula (I)

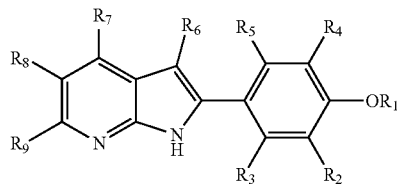

or a pharmaceutically acceptable salt and/or solvate thereof,
wherein:
$R_1$ is H, a $(C_1-C_6)$alkyl or a $(C_3-C_6)$cycloalkyl, or $R_1$ forms together with $R_2$ or $R_4$ a heterocycloalkyl;
$R_2$ and $R_3$ are H;
$R_4$ to $R_6$ are, independently of one another, H or $OR_{10}$;
$R_{10}$ is H or $(C_1-C_6)$alkyl;
$R_7$ is H or halo;
$R_8$ to $R_9$ are, independently of one another, H; halo; or a group selected from $(C_1-C_6)$alkyl, heterocycle, aryl, heteroaryl, —$(C_1-C_6)$alkyl-aryl, and —$(C_1-C_6)$alkyl-heterocycle, said group being optionally substituted with one or more groups selected from halo, —$OR_{36}$, —$NR_{37}R_{38}$, —$SR_{39}$, —$S(O)R_{40}$, —$SO_2R_{41}$, —$SO_2NR_{42}R_{43}$, —$OCOR_{44}$, —$NR_{45}COR_{46}$, —$NR_{47}C(O)OR_{48}$, —$CO_2R_{49}$, —$CONR_{50}R_{51}$, —$OCONR_{53}R_{54}$, —$COR_{55}$, nitro (—$NO_2$), cyano (—CN), oxo (═O), and a group selected from aryl, heterocycle and —$(C_1-C_6)$alkyl-heterocycle, said group being optionally substituted with one or more $(C_1-C_6)$-alkyl; and
$R_{36}$ to $R_{55}$ are, independently of one another, H, halo, benzoylbenzyl, or a group selected from $(C_1-C_6)$alkyl, aryl, heteroaryl, heterocycle, —$(C_1-C_6)$alkyl-heterocycle, and —$(C_1-C_6)$alkyl-aryl, said group being optionally substituted with one or more groups selected from halo, $CF_3$ and $(C_1-C_6)$alkyl; or $R_{37}$-$R_{38}$, $R_{42}$-$R_{43}$, $R_{50}$-$R_{51}$, and/or $R_{53}$-$R_{54}$ may together respectively form a heterocycloalkyl.

2. The method according to claim 1, wherein:
$R_1$ is H, a $(C_1-C_6)$alkyl or a $(C_3-C_6)$cycloalkyl, or $R_1$ forms together with $R_2$ or $R_4$ a heterocycloalkyl;
$R_2$ and $R_3$ are H;
$R_2$ to $R_6$ are, independently of one another, H or $OR_{10}$;
$R_{10}$ is H or $(C_1-C_6)$alkyl;
$R_7$ is H or halo;
$R_8$ is H; halo; or a group selected from $(C_1-C_6)$alkyl, heterocycle, aryl, heteroaryl, —$(C_1-C_6)$alkyl-aryl, and —$(C_1-C_6)$alkyl-heterocycle, said group being optionally substituted with one or more groups selected from halo, —$OR_{36}$, —$NR_{37}R_{38}$, —$SR_{39}$, —$S(O)R_{40}$, —$SO_2R_{41}$, —$SO_2NR_{42}R_{43}$, —$OCOR_{44}$, —$NR_{45}COR_{46}$, —$NR_{47}C(O)OR_{48}$, —$CO_2R_{49}$, —$CONR_{50}R_{51}$, —$OCONR_{53}R_{54}$, —$COR_{55}$, nitro (—$NO_2$), cyano (—CN), oxo (═O), and a group selected from aryl, heterocycle and —$(C_1-C_6)$alkyl-heterocycle, said group being optionally substituted with one or several-more $(C_1-C_6)$-alkyl;
$R_9$ is H; halo; or a group selected from $(C_1-C_6)$alkyl, aryl and heteroaryl, said group being optionally substituted with one or more groups selected from halo, —$OR_{36}$, —$NR_{37}R_{38}$, —$SR_{39}$, —$S(O)R_{40}$, —$SO_2R_{41}$, —$SO_2NR_{42}R_{43}$, —$OCOR_{44}$, —$NR_{45}COR_{46}$, —$NR_{47}C(O)OR_{48}$, —$CO_2R_{49}$, —$CONR_{50}R_{51}$, —$OCONR_{53}R_{54}$, —$COR_{55}$, nitro (—$NO_2$), cyano (—CN), oxo (═O), and a group selected from aryl, heterocycle and —$(C_1-C_6)$alkyl-heterocycle, said group being optionally substituted with one or more $(C_1-C_6)$-alkyl;
$R_{36}$ to $R_{55}$ are, independently of one another, H, halo, benzoylbenzyl, or a group selected from $(C_1-C_6)$alkyl, aryl, heteroaryl, heterocycle, —$(C_1-C_6)$alkyl-heterocycle, and —$(C_1-C_6)$alkyl-aryl, said group being optionally substituted with one or more groups selected from halo, $CF_3$ or $(C_1-C_6)$alkyl; or $R_{37}$-$R_{38}$, $R_{42}$-$R_{43}$, $R_{50}$-$R_{51}$, and/or $R_{53}$-$R_{54}$ may together respectively form a heterocycloalkyl.

3. The method according to claim 1, wherein $R_8$ to $R_9$ are, independently of one another, H; halo; or a group selected from $(C_1-C_6)$alkyl, piperidinyl, morpholinyl, pyrrolidinyl, phenyl, benzyl, thiophenyl, benzimidazolyl or imidazolyl, said group being optionally substituted with one or two groups selected from halo, —$OR_{36}$, —$NR_{37}R_{38}$, —$SR_{39}$, —$S(O)R_{40}$, —$SO_2R_{41}$, —$SO_2NR_{42}R_{43}$, —$OCOR_{44}$, —$NR_{45}COR_{46}$, —$NR_{47}C(O)OR_{48}$, —$CO_2R_{49}$, —$CONR_{50}R_{51}$, —$OCONR_{53}R_{54}$, —$COR_{55}$, nitro (—$NO_2$), cyano (—CN), oxo (═O), —$(C_1-C_6)$alkyl-heterocycle, and an heterocycle group.

4. The method according to claim 1, wherein $R_8$ to $R_9$ are, independently of one another, H, halo, or a phenyl group, said phenyl group being optionally substituted with one or two groups selected from halo, —$OR_{36}$ and —$(C_1-C_6)$alkyl-heterocycle.

5. The method according to claim 1, wherein:
$R_7$ is H or halo;
$R_8$ and $R_9$ are, independently of one another, H, halo, or a phenyl group, said phenyl group being optionally substituted with one or two groups selected from halo or —$OR_{36}$.

6. The method according to claim 1, wherein $R_3$, $R_5$ and $R_6$ are H.

7. The method according to claim 1, wherein $R_{36}$ to $R_{55}$ are, independently of one another, H, halo, or a group selected from $(C_1-C_6)$alkyl, aryl, heteroaryl, said group being optionally substituted with one or more groups selected from halo, $CF_3$ or methyl.

8. The method according to claim 1, wherein the compound is selected from the following compounds:

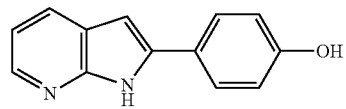

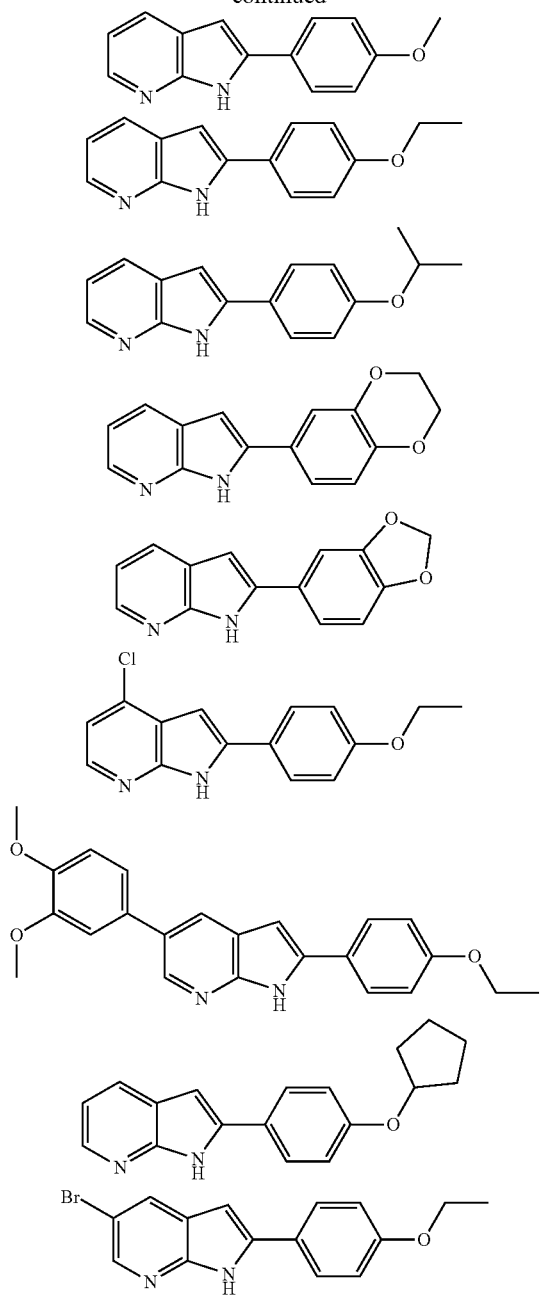

and the pharmaceutically acceptable salts and solvates thereof.

9. The method according to claim 1, wherein the compound is selected from the following compounds:

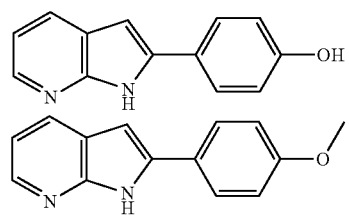

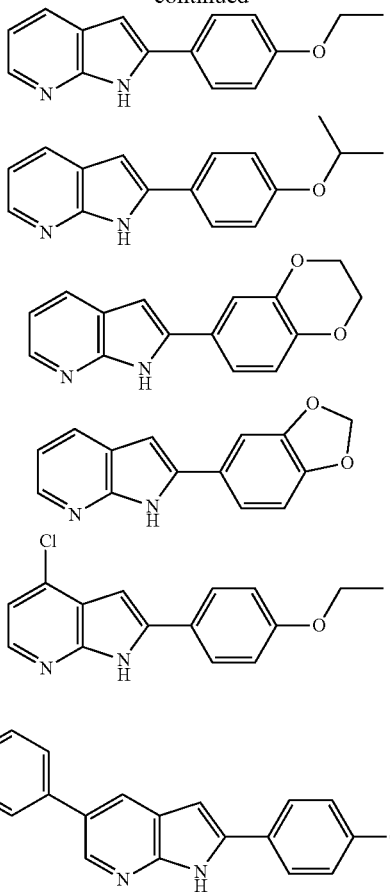

and the pharmaceutically acceptable salts and solvates thereof.

10. The method according to claim 1, wherein said pharmaceutically acceptable salts of the compound of general formula (I) are hydrobromic acid addition salts.

11. The method according to claim 1, wherein the patient has a disorder selected from trauma in brain, hepatitis, alcoholic and non-alcoholic steatohepatitis, acute pancreatitis and acute tubular necrosis, heart or kidney transplantation, atherosclerosis, bone marrow failure, viral infection, Crohn's and ulcerative colitis, terminal ileitis, chronic obstructive pulmonary disease or ischemia reperfusion injury.

12. The method according to claim 1, wherein the patient has a disorder selected from tumour cells extravasation or metastasis.

13. The method according to claim 1 wherein said compound of formula (I) is administered to said patient as a pharmaceutical composition comprising at least one pharmaceutically acceptable excipient.

14. The method according to claim 13, wherein the patient has a disorder selected from trauma in brain, hepatitis, alcoholic and non-alcoholic steatohepatitis, acute pancreatitis and acute tubular necrosis, heart or kidney transplantation, atherosclerosis, bone marrow failure, viral infection, Crohn's and ulcerative colitis, terminal ileitis, chronic obstructive pulmonary disease or ischemia reperfusion injury.

15. A method for the preservation and/or protection of biological materials comprising placing said biological materials in a medium containing a compound of the following general formula (I)

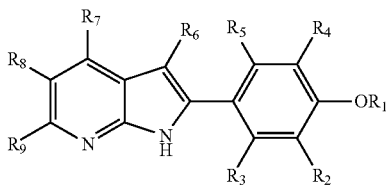

or a pharmaceutically acceptable salt and/or solvate thereof,
wherein:
- $R_1$ is H, a $(C_1-C_6)$alkyl or a $(C_3-C_6)$cycloalkyl, or $R_1$ forms together with $R_2$ or $R_4$ a heterocycloalkyl;
- $R_2$ to $R_6$ are, independently of one another, H or $OR_{10}$; $R_{10}$ is H or $(C_1-C_6)$alkyl;
- $R_7$ to $R_9$ are, independently of one another, H; halo; or a group selected from $(C_1-C_6)$alkyl, heterocycle, aryl, heteroaryl, —$(C_1-C_6)$alkyl-aryl, and —$(C_1-C_6)$alkyl-heterocycle, said group being optionally substituted with one or more groups selected from halo, —$OR_{36}$, —$NR_{37}R_{38}$, —$SR_{39}$, —$S(O)R_{40}$, —$SO_2R_{41}$, —$SO_2NR_{42}R_{43}$, —$OCOR_{44}$, —$NR_{45}COR_{46}$, —$NR_{47}C(O)OR_{48}$, —$COR_{49}$, —$CONR_{50}R_{51}$, —$OCONR_{53}R_{54}$, —$COR_{55}$, nitro (—$NO_2$), cyano (—CN), oxo (=O), and a group selected from aryl, heterocycle and —$(C_1-C_6)$alkyl-heterocycle, said group being optionally substituted with one or more $(C_1-C_6)$-alkyl; and
- $R_{36}$ to $R_{55}$ are, independently of one another, H, halo, benzoylbenzyl, or a group selected from $(C_1-C_6)$alkyl, aryl, heteroaryl, heterocycle, —$(C_1-C_6)$alkyl-heterocycle, and —$(C_1-C_6)$alkyl-aryl, said group being optionally substituted with one or more groups selected from halo, $CF_3$ or $(C_1-C_6)$alkyl; or $R_{37}$-$R_{38}$, $R_{42}$-$R_{43}$, $R_{50}$-$R_{51}$, and/or $R_{53}$-$R_{54}$ may together respectively form a heterocycloalkyl.

16. The method according to claim 2, wherein $R_1$ is H, a $(C_1-C_3)$alkyl or $R_1$ forms together with $R_2$ or $R_4$ a heterocycloalkyl.

17. The method according to claim 3, wherein $R_8$ to $R_9$ are, independently of one another, H; halo; or a group selected from $(C_1-C_6)$alkyl, piperidinyl, morpholinyl, pyrrolidinyl, phenyl, benzyl, thiophenyl, benzimidazolyl or imidazolyl, said group being optionally substituted with one or two groups selected from —$OR_{36}$, —$NR_{37}R_{38}$, —$OCOR_{44}$, —$NR_{45}COR_{46}$, —$NR_{47}C(O)OR_{48}$, —$CO_2R_{49}$, —$CONR_{50}R_{51}$, —$OCONR_{53}R_{54}$, —$COR_{55}$, —$(C_1-C_6)$alkyl-heterocycle or an heterocycle group.

18. The method according to claim 3, wherein $R_8$ to $R_9$ are, independently of one another, H; halo; or a group selected from $(C_1-C_6)$alkyl, piperidinyl, morpholinyl, pyrrolidinyl, phenyl, benzyl, thiophenyl, benzimidazolyl or imidazolyl, said group being optionally substituted with one or two groups selected from —$OR_{36}$ or an —$(C_1-C_6)$alkyl-heterocycle group.

19. The method according to claim 11, wherein the ischemia reperfusion injury is associated with a myocardial infarction or a stroke.

20. The method according to claim 14, wherein the ischemia reperfusion injury is associated with a myocardial infarction or a stroke.

21. The method according to claim 15, wherein the biological materials are cells, tissues, body fluids, organs or microorganisms.

* * * * *